US006840955B2

(12) United States Patent
Ein

(10) Patent No.: US 6,840,955 B2
(45) Date of Patent: Jan. 11, 2005

(54) THERAPEUTIC APPARATUS

(76) Inventor: Robert J. Ein, 4044 Palmetto Springs Way, Lexington, KY (US) 40513

( * ) Notice: Subject to any disclaimer, the term of this patent is extended or adjusted under 35 U.S.C. 154(b) by 20 days.

(21) Appl. No.: 09/769,727

(22) Filed: Jan. 26, 2001

(65) Prior Publication Data

US 2002/0026226 A1 Feb. 28, 2002

Related U.S. Application Data

(60) Provisional application No. 60/205,564, filed on May 22, 2000, and provisional application No. 60/177,715, filed on Jan. 27, 2000.

(51) Int. Cl.[7] .................................................. A61F 7/00
(52) U.S. Cl. .......................... 607/108; 219/528; 62/3.5
(58) Field of Search ......................... 607/108, 96, 109, 607/111; 606/112; 219/528, 529, 549, 211, 212; 62/3.5, 3.2; 126/204, 400

(56) References Cited

U.S. PATENT DOCUMENTS

| 2,617,916 A | * | 11/1952 | Neidnig ...................... 219/528 |
| 2,938,356 A | * | 5/1960 | McInahon ..................... 62/3.5 |
| 2,991,627 A | * | 7/1961 | Suits ............................ 62/3.5 |
| 3,080,723 A | * | 3/1963 | Price ............................. 62/3.5 |
| 3,132,688 A | * | 5/1964 | Nowak .......................... 62/3.5 |
| 3,136,577 A | * | 6/1964 | Richard ......................... 62/3.5 |
| 3,648,469 A | * | 3/1972 | Chapman ..................... 165/46 |
| 3,865,116 A | * | 2/1975 | Brooks ........................ 607/104 |
| 3,956,902 A |   | 5/1976 | Fields, Jr. |
| 4,033,356 A |   | 7/1977 | Hara |
| 4,338,944 A |   | 7/1982 | Arkans |
| 4,383,414 A |   | 5/1983 | Beitner |
| 4,466,439 A | * | 8/1984 | Moore ......................... 607/109 |
| 4,470,263 A | * | 9/1984 | Lehovec et al. .............. 62/3.5 |
| 4,483,021 A |   | 11/1984 | McCall |
| 4,541,432 A |   | 9/1985 | Molina-Negro et al. |
| 4,633,062 A | * | 12/1986 | Nishida et al. ............. 219/212 |
| 4,741,338 A |   | 5/1988 | Miyamae |
| 4,846,176 A |   | 7/1989 | Golden |
| 4,860,748 A |   | 8/1989 | Chiurco et al. |
| 4,909,255 A |   | 3/1990 | Farin |
| 4,930,317 A | * | 6/1990 | Klein ........................... 62/3.3 |
| 5,097,828 A |   | 3/1992 | Deutsch |
| 5,169,384 A |   | 12/1992 | Bosniak et al. |
| 5,197,294 A |   | 3/1993 | Galvan et al. |
| 5,255,520 A |   | 10/1993 | O'Geary et al. |
| 5,257,623 A |   | 11/1993 | Karasev et al. |
| 5,358,513 A |   | 10/1994 | Powell et al. |
| 5,365,739 A |   | 11/1994 | Fetterly |
| 5,433,735 A |   | 7/1995 | Zanakis et al. |
| 5,601,618 A | * | 2/1997 | James .......................... 607/71 |
| 5,605,048 A |   | 2/1997 | Kozlov et al. |
| 5,653,741 A | * | 8/1997 | Grant .......................... 607/114 |
| 5,800,490 A |   | 9/1998 | Patz et al. |
| 5,895,418 A |   | 4/1999 | Saringer |
| 5,913,849 A | * | 6/1999 | Sundstrom et al. ......... 604/291 |
| 5,922,012 A |   | 7/1999 | Sakano |
| 5,970,718 A | * | 10/1999 | Arnold ......................... 62/3.5 |
| 5,987,892 A |   | 11/1999 | Watanabe et al. |
| 6,021,348 A | * | 2/2000 | James ........................... 607/3 |

(List continued on next page.)

FOREIGN PATENT DOCUMENTS

| DE | 3905570 | * | 8/1990 |
| JP | 9-135859 | * | 5/1997 |

Primary Examiner—John A. Jeffery

(57) ABSTRACT

A thermal apparatus includes a wrap adapted to be secured to the body surface of a user. At least one temperature sensor is mounted to the wrap to measure an actual temperature of the body surface, and at least one thermoelectric device is mounted to the wrap to selectively deliver heat to and remove heat from the body surface. The thermal apparatus further includes a control unit mountable to the wrap. The control unit receives the actual temperature of the body surface from the temperature sensor and communicates with the thermoelectric device to operate the thermoelectric device as one of a heater and a cooler, thereby achieving a desired temperature of the body surface.

35 Claims, 31 Drawing Sheets

U.S. PATENT DOCUMENTS 6,023,932 A * 2/2000 Johnston .................... 607/96
6,024,762 A * 2/2000 Gray ......................... 607/109
6,074,414 A * 6/2000 Haas et al. ................ 607/108
6,125,636 A * 10/2000 Taylor et al. .............. 62/3.5
6,362,740 B1 * 3/2002 Jung ......................... 340/584

* cited by examiner

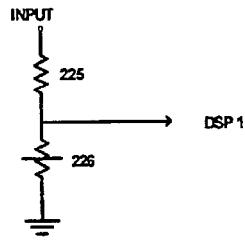
FIGURE 26 A
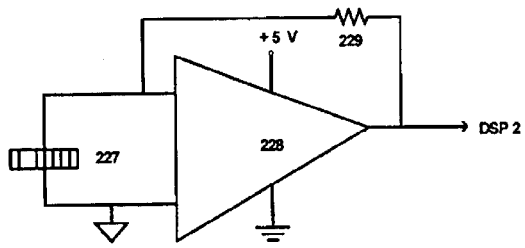
FIGURE 26 B
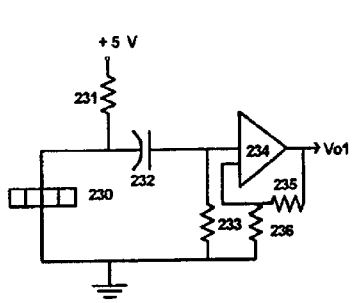
FIGURE 26 C
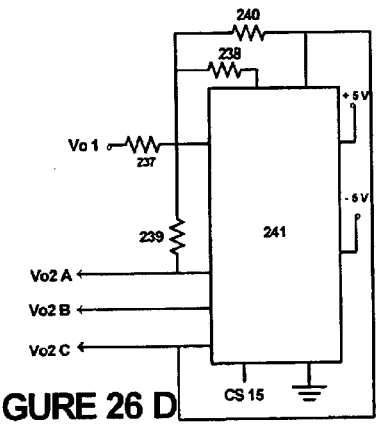
FIGURE 26 D
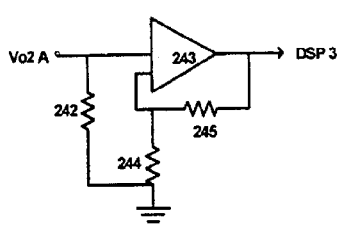   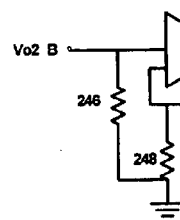   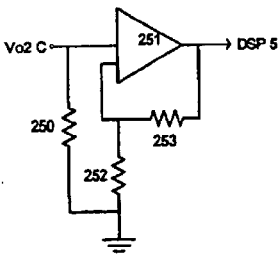
FIGURE 26 E   FIGURE 26 F   FIGURE 26 G

THERAPEUTIC APPARATUS

This application claims the benefit of U.S. Provisional Application No. 60/205,564, filed May 22, 2000, incorporated by reference herein in its entirety, and also claims the benefit of U.S. Provisional Application No. 60/177,715, filed Jan. 27, 2000.

BACKGROUND OF THE INVENTION

This invention relates to a portable therapeutic apparatus for use by humans, equines, and other animals. More specifically, this invention relates to a portable therapeutic apparatus for heating and cooling a body surface of a user, and, in some embodiments, non-invasive medical data collection and analysis, medicinal application, and electric stimulation to the surface of the user.

Various therapeutic devices have been developed in the past for treating muscle and tissue injuries. The types of treatment include heating, cooling, iontophoresis, or electrically stimulating an injured area. For example, for injuries requiring cold compresses, a cloth or bandage may be cooled in a freezer and applied to the injured area. Ice packs have also been used to apply cooling therapy to a body surface. For injuries requiring heat treatment, cloth or bandage may be heated in a microwave or oven and then applied to the injured area. Alternatively, heating pads or chemical salves may be applied to an injured area that requires heat therapy. U.S. Pat. No. 5,800,490, incorporated herein by reference in its entirety, provides a discussion of heating and cooling devices that have been used in the past for therapeutic purposes

BRIEF SUMMARY OF THE INVENTION

One embodiment of the therapeutic apparatus includes a wrap adapted to be secured to body surface of the user. The therapeutic apparatus also includes a portable power unit mountable to the wrap. At least one temperature sensor is mounted to the wrap to measure an actual temperature of the body surface, and least one thermoelectric (TE) device is mounted to the wrap to selectively deliver heat to and remove heat from the body surface. The therapeutic apparatus further includes a control unit mountable to the wrap. The control unit receives the actual temperature of the body surface from the temperature sensor and communicates with the TE device to operate the TE device as one of a heater and a cooler, thereby achieving a desired temperature of the body surface. The control unit is releasably mounted to the wrap so that it may be interchanged with another control unit. In this connection, the wrap preferably includes a receptacle or pocket therein for carrying the control and power units. The receptacle or pocket has a first port that communicates with temperature sensor and the TE device, and the control unit includes a second port for releasable connection with the first port. When the control unit is mounted to the wrap, the control unit can transmit information to the TE device and receives information from the temperature sensor. The first and second ports may comprise connector plugs. When removed from the wrap, the control unit may be plugged into a remote computer, via direct wiring or by a wireless connection, for updating, downloading of information, exchange of information, and other data transfer.

The control unit and the power unit can be combined into a single electronics package that is removably mounted to the wrap for connection with and disconnection from the TE device. The package can be interchanged with another package having different power unit and/or a different control unit. The power source can have a first identifier, and the control unit can have a second identifier, whereby the power source supplies power to the control unit only when the first identifier and the second identifier are compatible. In addition, the electronics package can be sealed so that the wrap can be immersed in water or other liquid and so that the electronics package is weather, germ and sweat proof.

In addition to the temperature sensor, the wrap can include a pressure sensor. The pressure sensor is adapted to turn the control unit on when the pressure sensor is activated. The pressure sensor can transmit information to the control unit.

In addition to the pressure sensor, the wrap can include a heart rate sensor. The heart rate sensor information can either be stored for delayed analysis or it can be transmitted to a remote data processing unit for real-time analysis and/or is adapted to turn off the control unit depending on the programming of the control unit and medical condition of the user.

In addition to the heart rate sensor, the wrap can include a breathing rate sensor. The breathing rate sensor information can either be stored for delayed analysis or it can be transmitted to a remote data processing unit for real-time analysis and/or is adapted to turn off the control unit depending on the programming of the control unit and medical condition of the user.

In addition, an evoked potential can be generated by deliberate stimulation of peripheral sense organs or their sensory nerves at any point along the sensory pathway. Evoked potentials differ from the spontaneous electrical activity that is transmitted within the nervous systems of both humans and animals in that they have a definite relationship to the onset of the stimulus and a constant pattern of response in relation to the neural structures being activated. This noninvasive technique allows for determination of functional status of major nerve circuits in the central nervous system.

The wrap includes an outer layer facing away from the body surface and an inner layer facing toward the body surface. The TE device is mounted between the outer and inner layers, and the temperature sensor is mounted to the inner layer to be nearer the body surface. The pressure sensor preferably is mounted to the inner layer of the wrap, while the receptacle for carrying the control unit preferably is disposed on the outer layer. The wrap may be attached to the body surface via a strap and/or straps, which generally is mounted to the outer layer of the wrap.

The wrap further includes two elastic layers. The first elastic layer is positioned between the outer layer and the TE device, and the second elastic layer is positioned between the TE device and the inner layer. The elastic layers provide cushioning to the therapeutic apparatus and enable the wrap to conform to the contours of the body surface. The TE device can be disposed in an insulate layer positioned between the first and second elastic layers. A first conductive layer is disposed between the first elastic layer and the first insulate layer, and a second conductive layer is disposed between the second elastic layer and the second insulate layer. The conductive layers contract the TE device to distribute a temperature to the first and second conductive layers, which, in turn, distribute a temperature to the environment and to the body surface, respectively. When one conductive layer is hot, the other is cool; this relationship occurs due to the Peltier effect of the TE device, which preferably is a Peltier device. The wrap further includes a wring/tubing layer is positioned between the two insulate layers The elastic layers are formed of a ventilated cushioning material. In addition, in one embodiment, at least one bladder layer is included. The first bladder layer is positioned between the outer insulate layer and the outer side of the wiring/tubing layer, and a second bladder layer is positioned between the inner insulate layer and the inner side of the wring/tubing layer. The bladder may be filled with fluid or air and expanded to increase the overall thickness of the wrap.

In another exemplary embodiment of the therapeutic apparatus, at least one electrode is provided on the inner layer of the wrap. The control unit activates the electrodes, can transmit electrical pulses to the body surface. The control unit is configured to enable to operate the TE device and the electrodes simultaneously or independently and, hence, both to achieve the desired temperature and to deliver electrical pulses to the body surface simultaneously or independently. The control unit is adapted to modify one of amplitude, frequency, and duration of the signal delivered to the electrodes, thereby modifying the electrical pulses delivered to the body surface. The control unit includes an electrical stimulation unit comprised of a waveform generator, modulator, driver, and the electrodes.

In another exemplary embodiment of the therapeutic apparatus, at least one special electrode is provided on the inner layer of the wrap. The control unit activates the special electrodes, which can transmit medication by means of iontophoresis to the body surface. The control unit is configured to enable to operate the TE device and the electrodes simultaneously and, hence, both to achieve the desired temperature of the body surface and to deliver iontophoresis to the body surface simultaneously. The control unit is adapted to modify one of medication dosage, dose rate, duration, and period of the signal delivered to the electrodes, thereby modifying the medication dose delivered to the body surface. The control unit includes an electrical stimulation unit comprised of a medication interface unit, medication controller, medication dispenser, and the special electrodes.

In another exemplary embodiment of the therapeutic apparatus, at least one special ultra miniature microphone is provided on the inner layer of the wrap. The control unit receives data from the special microphone, can amplify and filters this data and then digitizes this data and transfers the digitized data to the control unit. The control unit is adapted to store, transmit and/or process this digitized data. The control unit includes an evoked response detection unit comprised of a microphone, preamp, an active switched capacitor filter, and amplifiers. When a cell is excited, it generates an action potential, ionic current begins to flow. In the case of a nerve cell with a long axon, the action potential is generated over a very small segment of its length. As the action potential travels along the nerve fiber, it cannot reexcite the portion of the fiber immediately behind the advancing wave of depolarization because of the refractory period that follows the action potential. However, excitation of a nerve fiber somewhere along its length can produce an action potential propagated in both directions from the original point of excitation. The rate at which an action potential moves along a nerve fiber or is propagated from cell to cell is called the propagation rate. In nerve fibers, this is known as nerve conduction velocity. This velocity varies widely, depending on the type and diameter of the nerve fiber.

The basic elements of this technique include the electrodes for detecting electrical activity in the nervous system, the preamplifier stage that amplifies the signal, conditioning stage that filters the signal to reduce the amount of background interference, additional amplifier to increase the amplitude of the biologic signal of interest, digitizing and processing stages to average multiple responses, control and memory stage to capture and store the evoked response.

The control unit is configured to enable operation of the TE device, electrical stimulation, iontophoresis, and an evoked response used to measure medical parameters. These functions can be performed simultaneously, in combination, or independently. Hence, the control unit can achieve the desired temperature, can deliver electrical stimulation, iontophoresis, and an evoked response(s), and can analyze the user simultaneously.

The control unit of the therapeutic apparatus generally includes a controller, a first switch, and a second switch. The controller controls a desired temperature to be delivered to the body surface. The first switch, responsive to the actual temperature detected by the temperature sensor, disconnects the power unit when the actual temperature is above a maximum temperature or below a minimum temperature. The second switch communicates with the TE device to control the direction of current through the TE device and, hence, its operation as a heater or a cooler. The TE device is connected to the control unit to receive a signal from the controller corresponding to the desired temperature. The TE device delivers heating or cooling to the body surface in response to the desired temperature.

The controller can comprise a microprocessor. The microprocessor has memory that stores at least one program for adjusting the desired temperature to be delivered to the body surface over time. User identification information and clinician identification information can also be stored in the memory. The microprocessor also can include an input/output interface that enables modification of time and temperature parameters of the stored program to create a user-defined program. This input/output interface can be provided by the first port or plug connector, discussed above. In another aspect of the therapeutic apparatus, more suited for contexts where alteration of the stored programs by the user is denied, several programs can be stored in the microprocessor memory, and a user can select one from among several stored programs via the input/output interface. The stored programs have different time and temperature parameters so that the course and duration of heat and cold applied to the body surface varies between programs. This latter alternative provides flexibility through selection of different stored programs, but not through alteration of the stored programs.

The microprocessor has memory that stores at least one program for providing electrical stimulation to be delivered to the body surface over time. The microprocessor also can include an input/output interface that enables modification of time and duration of the electrical stimulation parameters of the stored program to create a user-defined program. The stored programs have different time and duration parameters so that the course and duration of electrical stimulation applied to the body surface varies between programs.

The microprocessor has memory that stores at least one program for providing iontophoresis medication to be delivered to the body surface over time. The microprocessor also can include an input/output interface that enables modification of dosage, dose rate, duration, and period of the iontophoresis medication parameters of the stored program to create a user-defined program. The stored programs have different time and duration parameters so that the dosage, dose rate and duration of iontophoresis medication applied to the body surface varies between programs.

The microprocessor has memory that stores at least one program for providing heating and cooling, electrical stimulation and/or iontophoresis medication simultaneously, combination, independently or staggered mode to be delivered to the body surface over time. The microprocessor also can include an input/output interface that enables modification of time and duration of the electrical stimulation parameters of the stored program to create a user-defined program. The stored programs have different time and duration parameters so that the course and duration of heating and cooling, electrical stimulation, iontophoresis medication, evoked response(s) analysis, and/or user medical condition simultaneously, combination, independently or staggered mode applied to the body surface varies between programs.

The microprocessor has memory that stores at least one program for providing evoked response detection of portions the user's central nervous system for evaluation. The microprocessor also can include an input/output interface that enables modification of treatment of the user or discontinuity.

The first switch of the control unit preferably is a digital thermostat. The temperature sensor is connected either to this digital thermostat or, in embodiments using a microprocessor, to the microprocessor. The control unit can also include a current limiting circuit/device in the current path of the TE device. The current limiting circuit/device controls the amount of current passing through the TE device.

The power unit includes a power source, such as a battery or a fuel cell, and an on/off switch for activating and deactivating the power source. The on/off switch, is some embodiments, is the pressure sensor; that is, the on/off switch comprises a pressure sensor switch. The power unit also includes a voltage limiting circuit/device, in parallel with the power source and the on/off switch, to control the voltage delivered by the power source.

The therapeutic apparatus can also include a heart rate for detecting a user's heart rate. The heart rate sensor communicates heart rate information to the control unit. Further, the therapeutic apparatus can include a breathing rate sensor for communicating breathing rate signals to the control unit, and for the therapeutic apparatus can also include a blood pressure sensor for communicating blood pressure signals to the control unit and, for the therapeutic apparatus can also include a motion sensor for communicating body motion signals to the control unit.

The therapeutic apparatus includes a data link unit, such as a connector for transfer of information to and from the microprocessor. The microprocessor communicates information to and from the control unit. Further, the therapeutic apparatus can include an IR or RF wireless transceiver to communicate directly with a remote computer, signals to and from the control unit.

The therapeutic apparatus includes a remote control unit, such as a remote computer for processing of information to and from the apparatus microprocessor. The microprocessor communicates information to and from the its control unit to the remote control unit. Further, the therapeutic apparatus microprocessor can receive programming instructs directly from the remote control unit.

BRIEF DESCRIPTION OF THE DRAWINGS

Other objects and advantages of the present invention will become apparent from the following detailed description of the preferred embodiment of thereof taken in conjunction with the accompanying drawings, wherein:

FIG. 26A is a schematic of the Temperature Sensor for the Heating/Cooling embodiment of the invention;

FIG. 26B is a schematic of the Pressure Sensor for the Alignment embodiment of the invention;

FIG. 26C is a schematic of the Microphone/Preamp Sensor for the Evoked Response Detection embodiment of the invention;

FIG. 26D is a schematic of the Active Filter Stage for the Evoked Response Detection embodiment of the invention;

FIG. 26E is a schematic of the Amplifier Stage of the Low-pass Signal for the Evoked Response Detection embodiment of the invention;

FIG. 26F is a schematic of the Amplifier Stage of the High-pass Signal for the Evoked Response Detection embodiment of the invention;

FIG. 26G is a schematic of the Amplifier Stage of the Bandpass Signal for the Evoked Response Detection embodiment of the invention;

DETAILED DESCRIPTION OF THE INVENTION

The present invention relates to a portable therapeutic apparatus for heating and cooling the body surface of a user, and, in some embodiments, for applying electrical stimulation and iontophoresis medication to the body of the user. The therapeutic apparatus may be applied to humans, equines, or other animals and is configured to meet the specific demands of the user. For example, the therapeutic apparatus can form part of a horse blanket when used with equines.

The therapeutic apparatus of the present invention has several applications. For example the therapeutic apparatus can be used as a therapeutic device to supply heat or coolness to a targeted body surface of the user and, in some embodiments, electrical stimulation and iontophoresis medication to the body surface to treat various medical ailments and conditions. The apparatus can also be used as an analgesic, or, in a simpler, a healthy person to supply warmth or coolness to the person's body can, also use more leisurely context. In addition, the therapeutic apparatus can be incorporated into an outer garment to provide thermal control, protection, and comfort in extreme environments. These applications are available in a safe, easy to operate, lightweight, rugged, portable apparatus that does not create electrical interference with other electronic devices and that it is usable in most environments. These applications and advantages will become clearer in the detailed description below.

Figure 1:
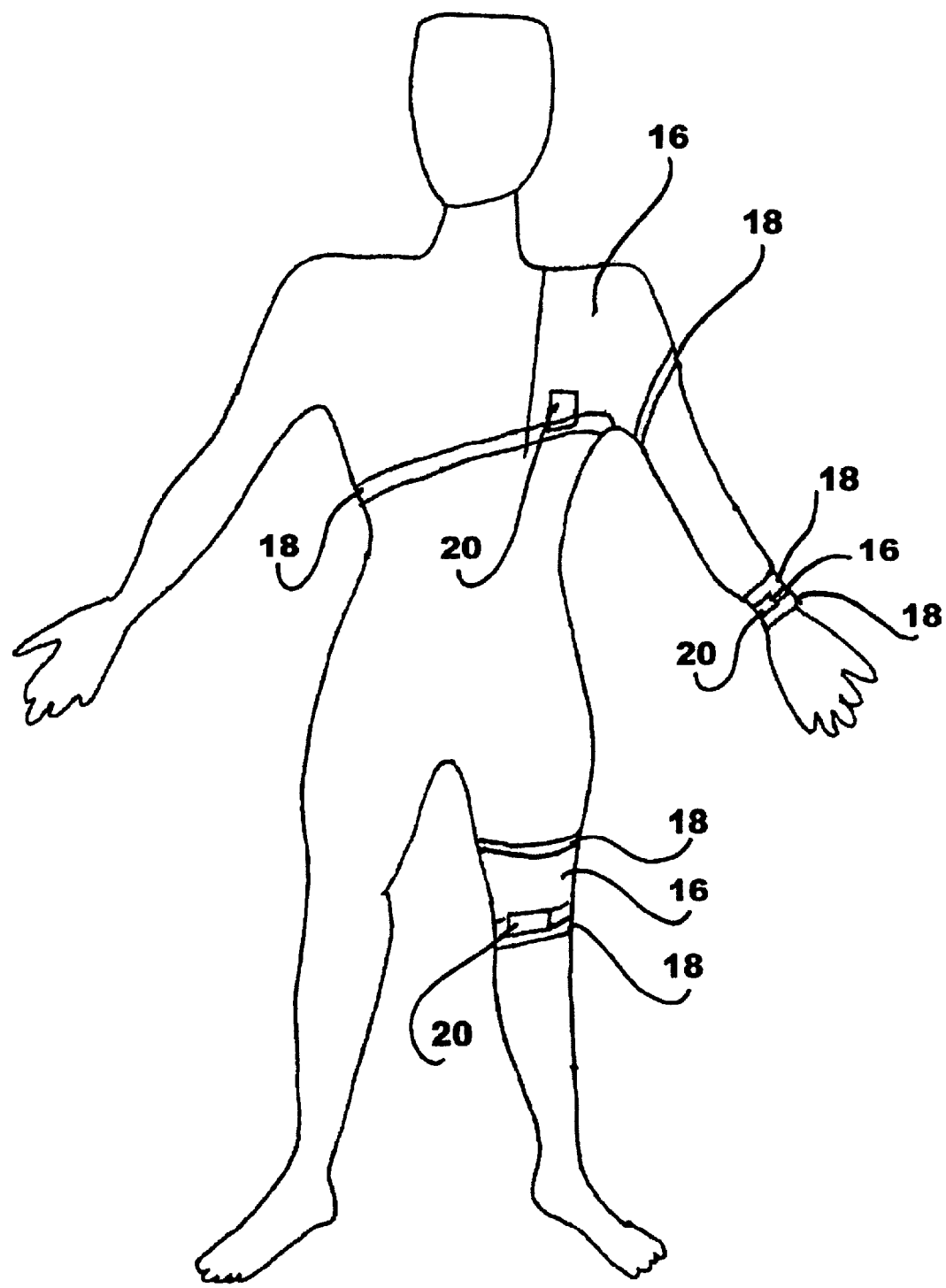
FIG. 1 is a schematic disclosing a context of the invention and depicts a user wearing knee, wrist, and shoulder embodiments of the therapeutic apparatus in accordance with the invention.

Referring now to the drawings, wherein identical numerals indicate identical parts, and initially to FIG. 1, there will be seen an operative context of the present invention. More particularly, a person shown wearing several therapeutic apparatuses in accordance with the present invention. Therapeutic apparatus 10 is applied to the person's shoulder; therapeutic apparatus 12 is applied to the person's wrist; and therapeutic apparatus 14 is applied to the person's knee. As evident from FIG. 1, the therapeutic apparatus of the present invention may be mounted to various body surfaces of the person. In another context, the therapeutic apparatus can be mounted to horse blanket or other animal clothing or wraps.

Each therapeutic apparatus generally includes a wrap 16 adapted to be secured to the target body surface. Wrap will be understood to encompass any item that may be worn or carried on a user's body, including bandages, harnesses, appliques, outer clothing garments, under garments, shawls, and blankets. When in the forms of appliques or horse blankets, the wrap can be easily secured to animals, particularly equines. The wrap 16 may be formed in various shapes to fit the contours of the target body surface. For example, the wrist and knee wraps comprise rectangularly shaped strips that can encircle the appropriate body part, whereas the shoulder wrap includes a sleeve area for mounting over the person's shoulder and down the person's upper arm.

A glove wrap has been contemplated to provide penetrating cold to the user's hand for therapeutic relief from surgery to treat medical conditions including Carpal Tunnel Syndrome, Trigger Finger, or Dupuytren's Contraction. The glove wrap can also provide heat to the user's hand to treat arthritis. The shoulder wrap 10 provides therapeutic cooling for shoulder injuries incurred in accidents (e.g., sports, vehicular, etc.) and therapeutic heating for medical conditions such as bursitis or arthritis. As an elbow wrap, the therapeutic apparatus can provide therapeutic cooling for elbow injuries incurred in accidents (e.g., sports, vehicular, etc.) and therapeutic heating for medical conditions such as arthritis. The knee wrap 14 provides therapeutic cooling for relief from swelling generated during surgical procedures, sport injuries, accidents, etc., and therapeutic heating for medical conditions such as arthritis or other inflammatory maladies. As a foot hip/groin, thigh, or neck/collar wrap, the therapeutic apparatus can provide therapeutic cooling for relief from swelling generated during surgical procedures, sport injuries, accidents, etc., and therapeutic heating for medical conditions such as circulatory conditions, arthritis or other inflammatory maladies. As a back wrap, the therapeutic apparatus can provide therapeutic cooling for relief from swelling and therapeutic heating to treat circulatory conditions, lower back spasms, arthritis or other inflammatory maladies. The therapeutic apparatus can also be configured as facemask to provide therapeutic cooling relief from sinus conditions, headaches, and migraines.

The wrap 16 preferably is secured to the body surface by one or more strap 18. The strap(s) 18 may be sewn to the wrap 16, with the exception of two loose ends hat tie together to bind the wrap 16 to the body surface. Alternatively, each strap may be secured to the wrap, and even secure to itself, by hook and loop fastening material. Other methods of securing the wrap to the body surface via straps are contemplated by this invention.

The wrap 16 preferably includes a receptacle or pocket 20 for carrying a removable control unit and a power unit, collectively an electronics package, of the therapeutic apparatus. It will be understood that the electronics package can be mounted to the wrap 16 by other mechanisms, such as clips or hook and loop fastening material. This removability of the electronics package from the wrap provides some advantages. For example, should the wrap become dirty or damaged, the wrap can be replaced, and the electronics package reused. Alternatively, should the electronics break at a time when the wrap is relatively new, a replacement electronics package can be replaced with another electronics package with different heating/cooling, electrical stimulation, and/or iontophoresis medication capabilities.

Figure 2:
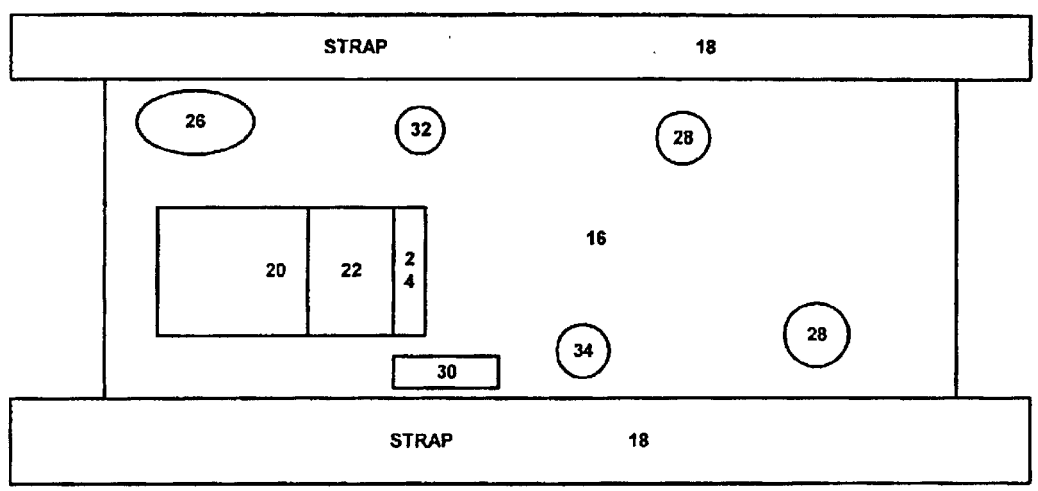
FIG. 2 is a schematic of a top view of the therapeutic apparatus wrap configuration.

Referring to FIG. 2, the electronics package may be inserted into pocket 20 for connection to a TE device and various sensors of the therapeutic apparatus to control heating and cooling, and, in some embodiments, electrical stimulation, iontophoresis medication, of the target body surface. The pocket 20 includes a flap 22 that may be pulled back at its edge 24 from the wrap 16 to open the pocket 20. The electronics package can then be slid into the pocket 20, where it sets in an inner chamber, defined by dashed lines underlying the pocket flap 22 in FIG. 2. The electronics package can be connected to a port 26, or connector plug, inside the pocket 20 to enable communication between the electronics package and the various sensors and electrodes of the therapeutic apparatus, which provide feedback to the electronics package and receive signals from the electronics package. The electronics package, which removably mounts to the wrap 16, may be interchanged with other packages. Because the electronics package is interchangeable, the wrap 16 may be reused in different applications. For example, one injury may require heating and cooling, and a first electronic package can be inserted into the pocket to deliver the required treatment, whereas a second injury may require heating and electrical stimulation and no cooling, and a second electronics package can be inserted into the pocket to deliver this different type of treatment. Operation and structure of the power unit and control unit will be described below in more detail in FIGS. 5–27. It will be understood that, in some embodiments of the therapeutic apparatus, the electronics package is permanently mounted to the wrap, and in other embodiments, only one or the other of the control unit and the power unit can be removed from the wrap, with the other permanently mounted to the wrap.

Figure 3:
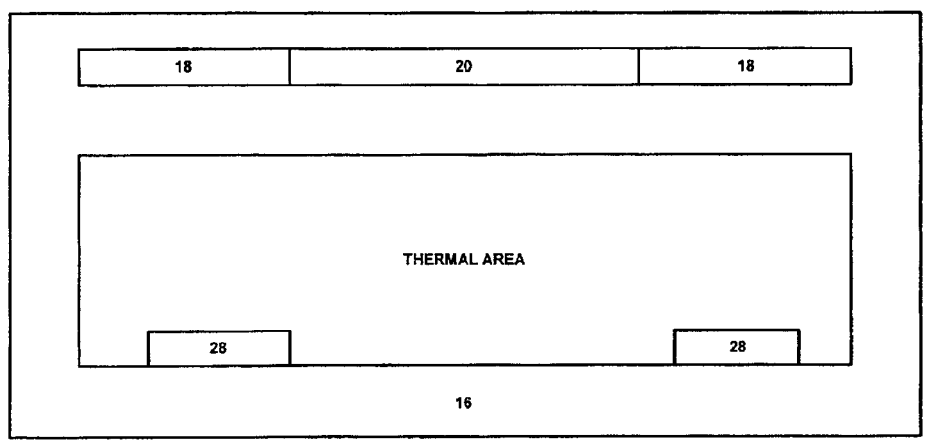
FIG. 3 is a schematic of an end view of the therapeutic apparatus wrap configuration.

FIGS. 2 and 3 show an embodiment of the therapeutic apparatus. The apparatus generally includes the wrap 16, at least one temperature sensor 28 mounted to the wrap 16 to measure an actual temperature of the body surface of the user, at least one TE device (here, shown as a thermal area or thermal plate 30 mounted to the wrap 16 to deliver a desired temperature to the body surface, and a power unit and control unit (not shown) removably mountable in the pocket 20 of the wrap 16. Heating or cooling depends in part on inputs to the control unit of the electronics package from the temperature sensors 28. The temperature sensors 28 provide feedback to the control unit; the control unit then adjusts the current applied to the TE device to deliver a current corresponding to the desired temperature required from the TE device.

The temperature sensors 28 preferably are located at several locations on the inner layer (i.e., skin side) of the wrap 16. The sensors 28 may be mounted between the thermal area 30 and an inner layer 36 and the user's skin. Although one pressure sensor 32 and two temperature sensors 28 are shown in FIG. 2, the number of sensors is application dependent. A larger thermal wrap would have more sensors, including pressure, temperature, pulse rate, blood pressure and/or breathing rate, than would a wrap of smaller dimension.

The electronics package of the therapeutic apparatus preferably is encased in a disposable or permanent liner for safety and sanitary considerations. In this manner, the same electronics package, including the power source and controller, can be used with multiple thermal wraps that have compatible identification. A mass-market version of the therapeutic apparatus could include the thermal and electronics package in a single assembly.

The present invention works on the principal of the efficient use of TE devices. By way of a brief overview, TE devices are solid state heat pump devices that exchange electrons from one source to another to maintain equilibrium. The present invention provides temperature stabilization, temperature cycling, or cooling/heating below/above the ambient temperature as required by the user. The TE devices of the present invention are based on the Peltier Effect, by which Direct Current (DC) applied across two dissimilar materials causes a temperature differential, and, hence, are called Peltier devices.

A TE device typically is manufactured using two thin ceramic wafers with a series of P and N doped semiconductor material sandwiched between the wafers. The wafers provide the stiffness and electrical isolation required for the invention. The N material has an excess of electrons and the P material has a deficiency of electrons. One P and one N make up a couple. These TE couples are electrically in series and thermally in parallel. Each TE device contains multiple couples. As the electrons move from the P material to the N through an electrical connector, the electrons jump to a higher energy state, absorbing thermal energy and creating a cooling effect at the wafer toward which the electrons move (i.e., the cold side). By comparison, as electrons flow through the lattice from the N material to the P material through an electrical connector, they drop to a lower energy state, thus releasing energy as heat to a heat sink and creating a heating effect at the wafer toward which the electrons move (i.e., the hot side) The present invention generates heating or the cooling, depending on the direction of the current flow within the TE device.

The appropriate TE device for any application depends on at least the following three parameters. These parameters are the hot surface temperature ($T_h$), the cold surface temperature ($T_c$), and the heat load to be absorbed at the cold surface ($Q_c$). The temperature difference across the TE device ($\Delta T$) relates to $T_h$ and $T_c$ in the following equation: $\Delta T = T_h - T_c$. Estimating $Q_c$, i.e., the heat load in watts absorbed from the cold side, is difficult because all thermal loads in the application design must be considered. Among these loads are: 1) Active $I^2R$ heat load from the TE device and other electronic devices; 2) Any load generated by a chemical reaction; 3) Passive radiation (heat loss between two close objects with different temperatures); 4) Convection (heat loss through the air, where the air has a different temperature than an adjunct object); 5) Insulation Loss; 6) Conduction Losses (heat loss through leads, screws, etc.); and 7) Transient Load (time required to change the temperature of an object). All TE devices are rated for $I_{max}$, $V_{max}$, $Q_{max}$ and $\Delta T_{max}$, at a specific value of $T_h$. Operating at or near the maximum power is relatively inefficient due to internal heating (Joulian Heat) at high power. Therefore, the TE device is operated somewhere between 25% to 80% of the maximum current. The input power to the TE device determines the hot side temperature cooling capability at a given load. As the TE device operates, the current flowing through it has two effects: 1) The Peltier Effect (cooling) and 2) The Joulian Effect (heating). The Joulian Effect is proportional to the square of the current. Therefore, as the current increases, the Joule heating dominates the Peltier cooling and causes a loss in net cooling. This cut-off defines $I_{max}$ for the TE device. For each device, $Q_{max}$ is the maximum heat load that can be absorbed by the cold side of the TE device. This maximum occurs at for $I_{max}$, $V_{max}$ and $\Delta T=0°$ C. The $\Delta T_{max}$ value is the maximum temperature difference across the TE device. This maximum occurs at $I_{max}$, $V_{max}$ and with no load ($Q_c=0$ watts).

The therapeutic apparatus of FIG. 2 also includes an on/off pressure sensor 32 mounted to the wrap 16. The on/off pressure sensor 32 operates to control communication between the electronics package and the TE device. When the wrap 16 is properly positioned on the user's body, causing a sufficient amount of pressure to be applied to the pressure sensor 32, the pressure sensor 32 turns on, and signals may be sent from the electronics package to the TE device and the temperature sensor(s) 28. In this manner, the pressure switch 32 operates as the therapeutic apparatus'on/off switch. Although only one pressure sensor 32 is shown in FIG. 2, it will be understood that more than one pressure sensor can be mounted on the wrap 16. The pressure sensors 32 are preferably mounted to the inner layer of the wrap 16 so that the pressure sensors 32 are positioned close to the user's skin; in this position, the pressure sensor is able to most accurately detect proper alignment of the wrap 16. If the wrap 16 is misaligned, then the pressure sensor 34 will not receive the proper amount of pressure, and the electronics package will not be able to communicate with the TE device 30 and, when present, electrodes, mounted to the wrap 16.

The therapeutic apparatus of FIG. 2 also includes a temperature limit switch 34, which will be described in more detail in connection with FIGS. 5–7. Generally, the temperature limit switch 34 controls the temperature range of heating or cooling that is generated by the TE device. In addition, the temperature limit switch 34 can ensure that excessive heating/cooling is not generated by the TE device in the thermal unit 30, should a current limiting circuit/unit within the power unit fail.

Heart rate, blood pressure, breathing rate, and motion sensors (not shown in FIGS. 2 and 3) also can be mounted to the wrap 16. Information detected by heart rate, blood pressure, breathing rate and motion sensors can be collected by the control unit in the electronics package and, in some embodiments, can be used to determine the amount of heating/cooling, electric stimulation and/or iontophoresis medication to be applied to the user.

FIGS. 4A–4E illustrate cross sections of several arrangements of the present invention for different portions of the user's body. For ease of illustration, the pocket of the wrap is not shown in FIGS. 4A–4E.

Figure 4A:
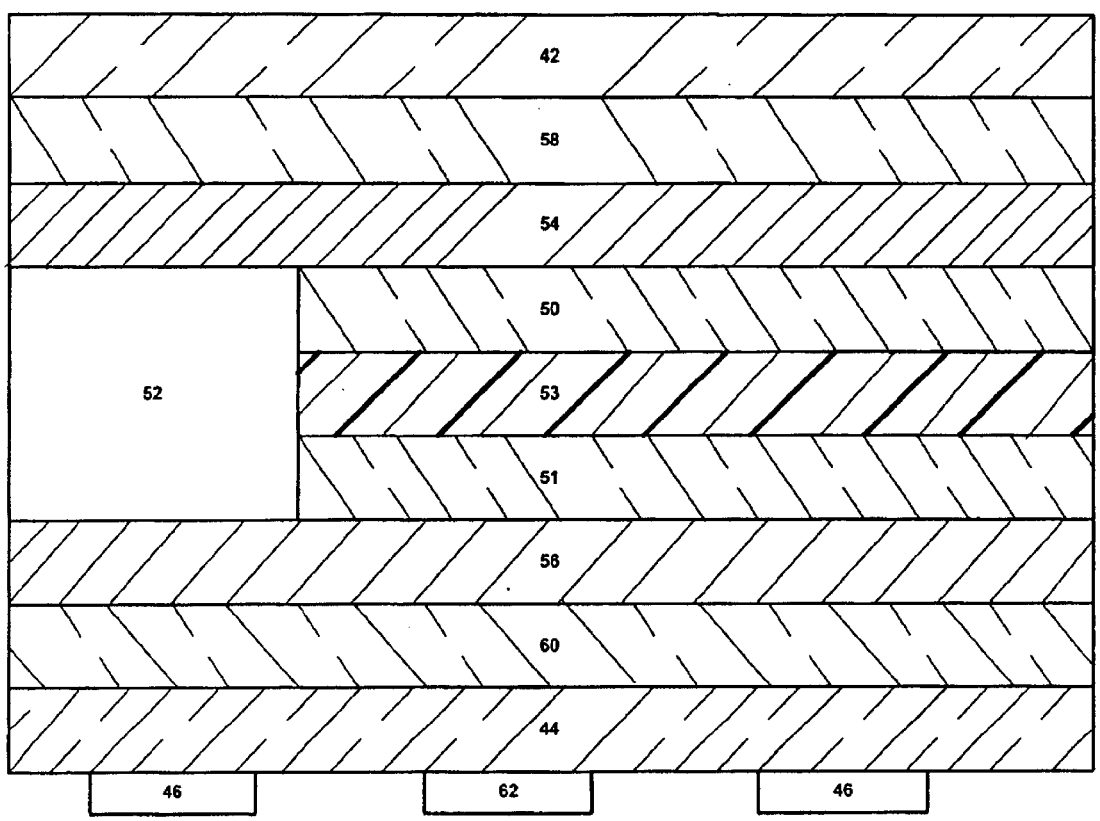
FIG. 4A is a cross section of the first arrangement of therapeutic apparatus wrap in accordance with the invention.

FIG. 4A shows an arrangement that may be used on a user's elbows, knees, thighs, shoulders, arms, feet, wrists, and back. The wrap generally includes an outer layer 42 facing away from the body surface and an inner layer 44 facing toward the body surface. These layers 42, 44 preferably are composed of ventilated reinforced material. Temperature sensors 46 are positioned on an inner surface 48 of the inner layer 44 so that they come into contact with the skin surface (or clothing surface in those instances that the wrap 40 overlies clothing items). The wrap 40 also includes a first insulate layer 50 and contact the outer wiring/tubing layer 53 and has embedded within the wiring/tubing layer the TE device 52 and a second insulate layer 51 which is in contact with the inner wiring/tubing layer 53. A first elastic layer 58 is disposed between the outer layer 42 and the first conductive layer 54, and a second elastic layer 60 is disposed between the inner layer 44 and the second conductive layer 56. These layers 58, 60 preferably are composed of a ventilated cushion material designed to enable the wrap to conform to the contours of the body surface to which the wrap 40 is attached.

The arrangement of FIG. 4A further includes at least one pressure sensor 62 that determines whether the wrap 40, and, consequently, the TE devices 52, are positioned properly on the user. If the invention is not properly positioned on the user, the pressure sensor 62 will not be activated, and the therapeutic apparatus will not operate. The pressure sensor 62 ensures that the wrap 40 is not improperly aligned with respect to the body surface of the user. Accordingly, heat and cooling will be applied only to a desired area.

The first, or outer, conductive layer 54 preferably has a greater surface area than the second, or inner, conductive layer 56. The outer conductive layer 54 may, for example, have a larger width dimension, than the inner conductive layer 56, as shown in FIG. 4A. The outer conductive layer 54 has a larger surface area than the inner conductive layer 56 so that, when the TE devices 52 are functioning in a cooling mode, heat generated at the outer conductive layer 54 is dissipated across a relatively large surface area. A difference in width is only one way to produce such a difference in surface area; for example, it will be understood that the outer conductive layer 54 can be made longer than the inner conductive layer 56. Other dimensions of the outer and inner conductive layers 54, 56 respectively, can be altered to result in a difference in surface area, and these structural alterations are contemplated by this invention.

Figure 4B:
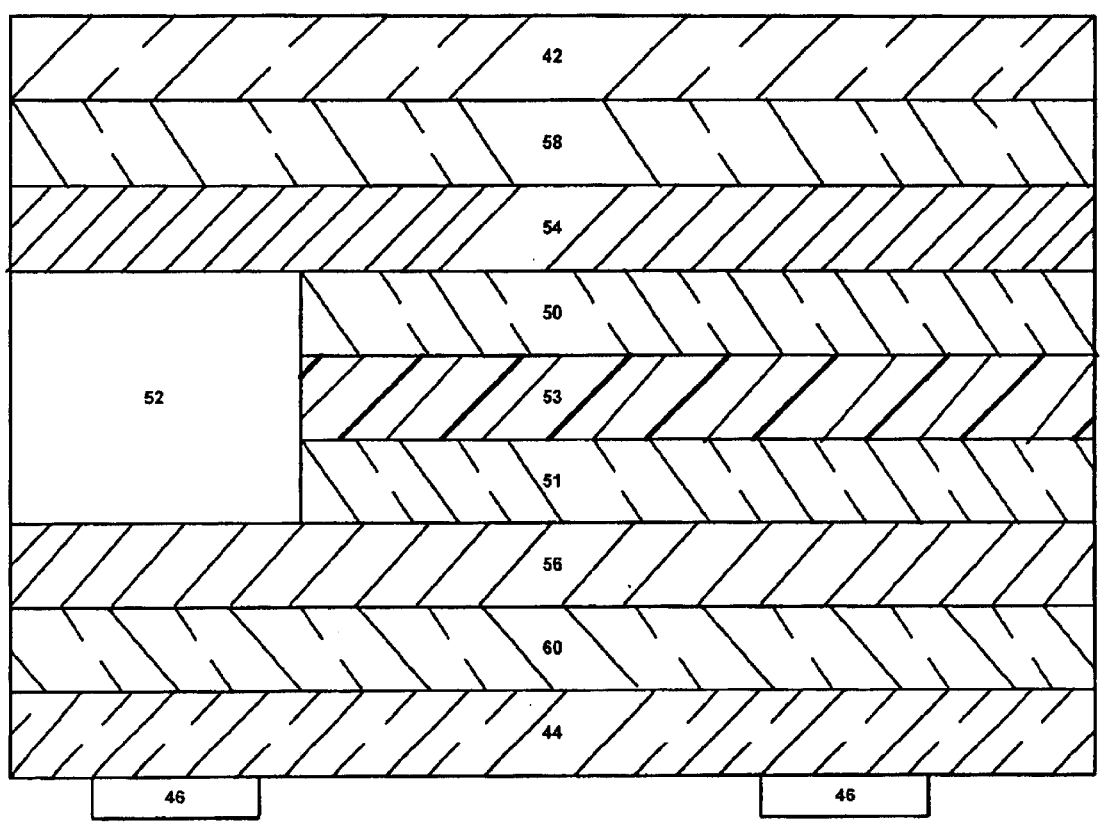
FIG. 4B is a cross section of the second arrangement of therapeutic apparatus wrap in accordance with the invention.

The arrangement of FIG. 4B may be used for ankle injuries, where compression is also required. FIG. 4B contains substantially the same structural features of FIG. 4A, with the exception of a pressure sensor 62.

Figure 4C:
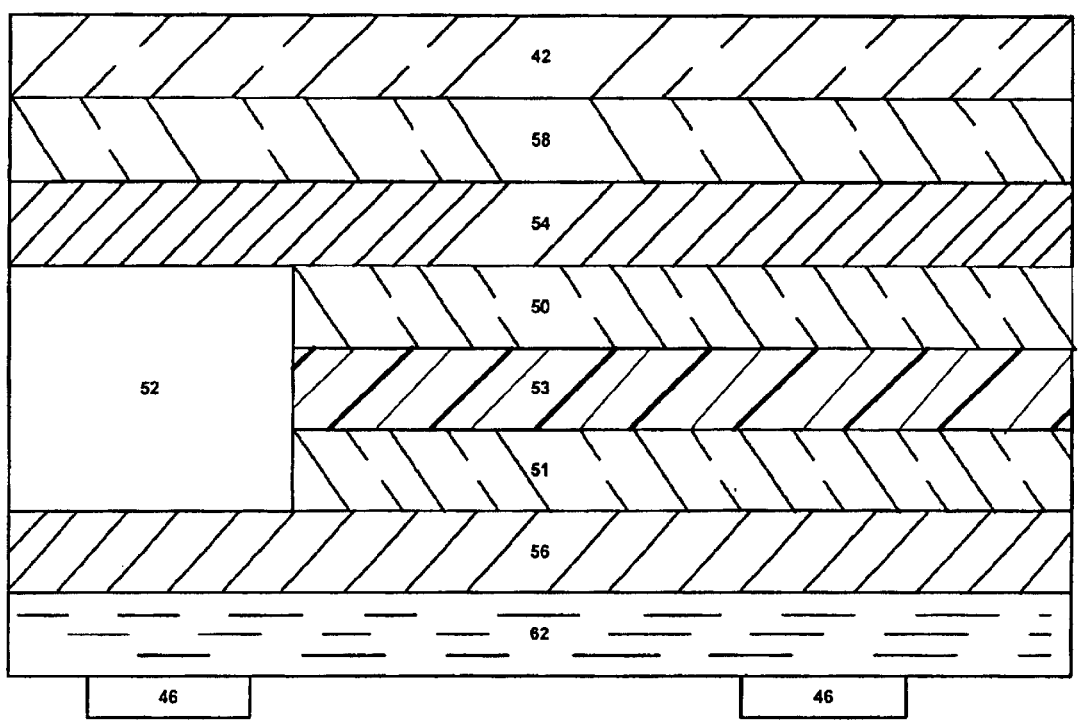
FIG. 4C is a cross section of the third arrangement of therapeutic apparatus wrap in accordance with the invention.

The arrangement of FIG. 4C preferably is used for facial and neck applications. In this embodiment, the second elastic layer 60 of ventilating cushion material and the inner layer 44 of ventilating reinforced material, shown in FIGS. 4A and 4B, are replaced with a fluid transfer medium layer 62. This fluid transfer medium layer 62 can be one or more of the following: air, flexible foil, conductive gel, liquid, and any other suitable conductive media. The fluid transfer medium layer 62 preferably comprises a fluid contained in a bladder. Temperature sensors 46 are mounted to the bladder. The fluid transfer medium layer 62 provides a comfortable surface for placement against a user's face and neck, which generally are sensitive areas.

Figure 4D:
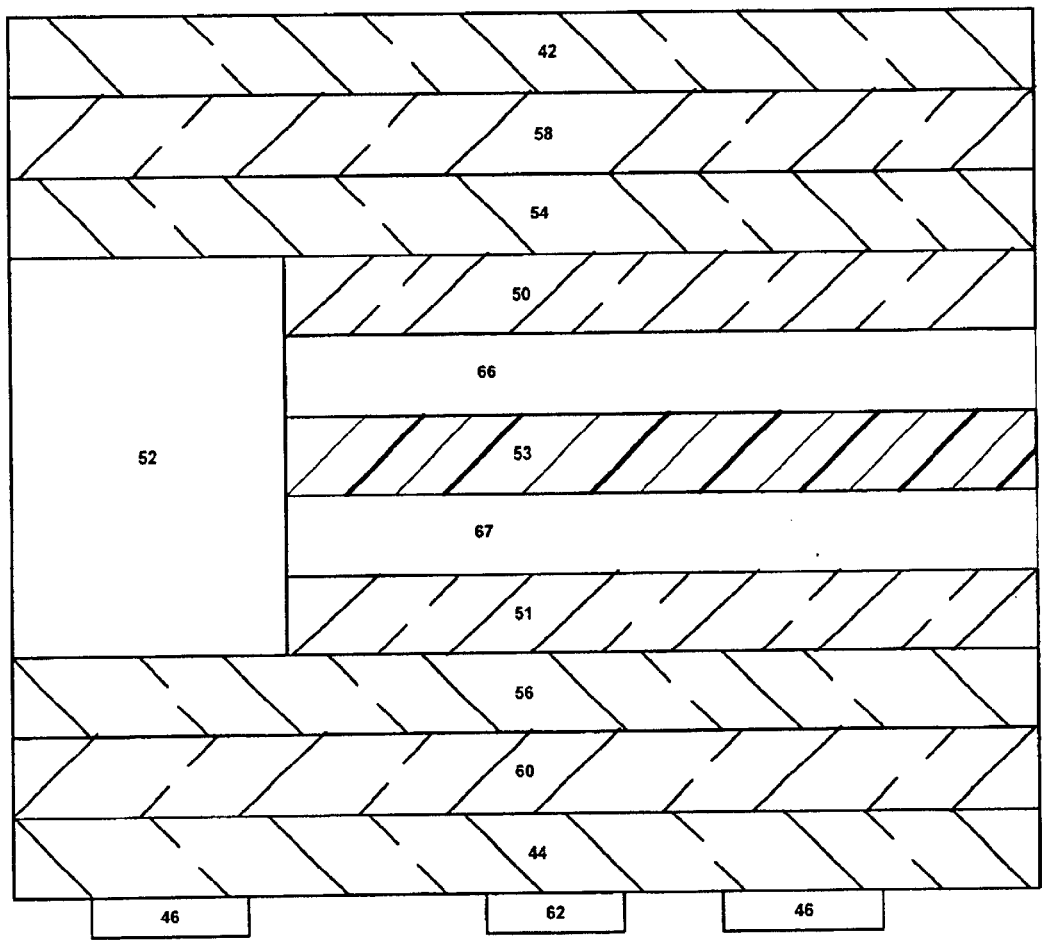
FIG. 4D is a cross section of the forth arrangement of therapeutic apparatus wrap in accordance with the invention.

The embodiment of FIG. 4D preferably is used when a cast is required in the medical treatment of the user. In such a case, the outer layer 42, the insulate layer 50, the first elastic cushion layer 58, and the outer layer 42, the insulate layer 50, the first elastic layer 58, and the outer conductive layer 54, and part of the wiring/tubing layer 53 are mounted to the outside of the cast. These layers are attached to the remaining portion of the therapeutic apparatus via a wick extension or strip line (not shown) that connects at one end to the TE devices 52 and the other end to the outer conductive layer 54. The strip line enables the outer conductive layer 54 to create a heat sink effect by which excessive heat/cold is vented to the outside of the cast.

Figure 4E:
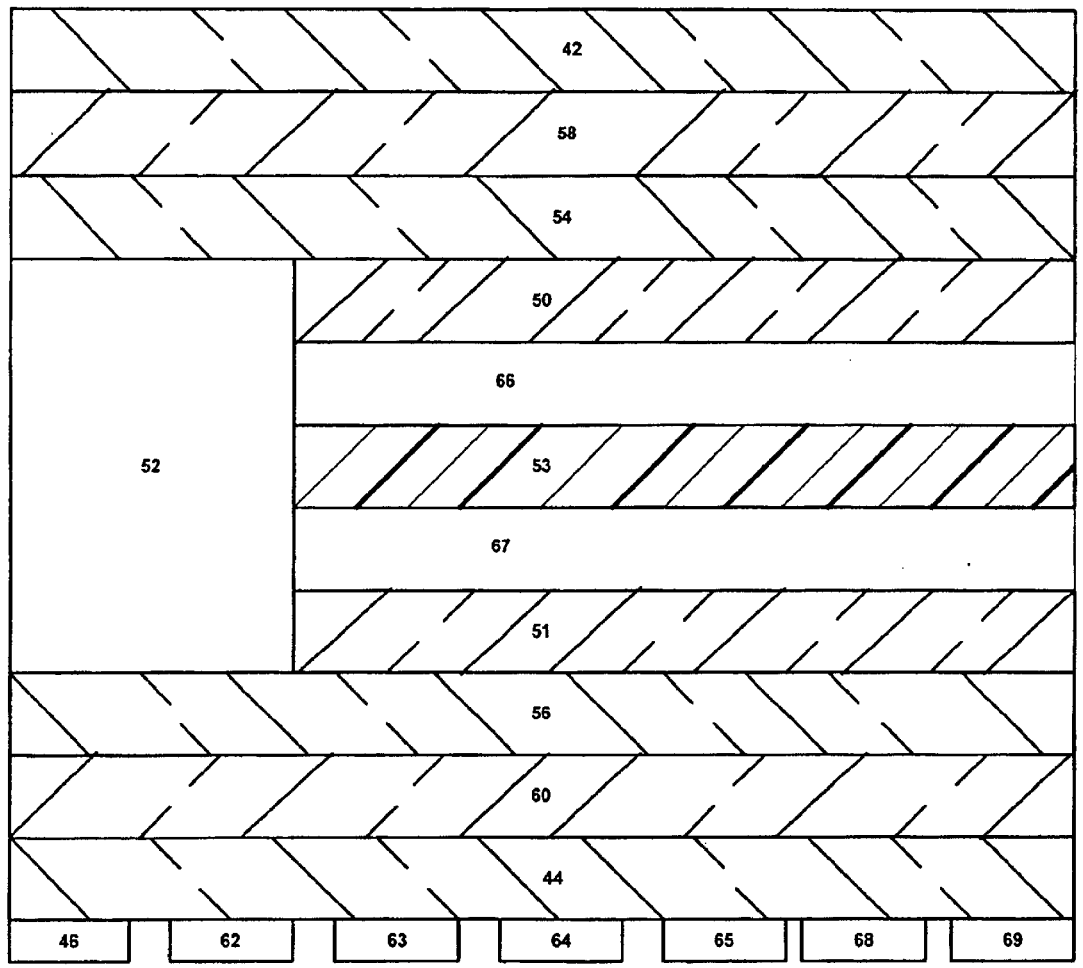
FIG. 4E is a cross section of the fifth arrangement of therapeutic apparatus wrap in accordance with the invention.

The embodiment of FIG. 4E is used when any or all of the following user's medical parameters are required in the operation of the apparatus: 1) temperature; 2) heart rate; 3) blood pressure; 4) breathing rate; and 5) evoked response. These parameters can be used to control the apparatus by certain programs within the apparatus. FIG. 4E includes the addition of sensor elements 65, 68, 69. When electrical stimulation is required electrode 64 is required and special electrodes 63 when iontophoresis medication is required as part of the treatment.

In addition, in the arrangement shown in FIG. 4D, the apparatus includes at least one expandable cavity 66, or pressure pouch/bladder, between the insulate layer 50 and the outer surface of the wiring/tubing layer 53 and a second pressure pouch, between insulate layer 51 and the inner surface of the wiring/tubing layer 53. The cavity 66 can be expanded when filled with fluid. FIG. 4D show a pair of pressure pouches/bladders 66, 67 connected by a fluid passage, such as a connecting tube, which can be attached to the wiring/tubing layer 53 tubing line(s). The inclusion of pressure pouches/bladders 66, 67 is particularly suited to embodiments designed for use with a cast. When an appendage is broken, the appendage typically swells. A cast is placed on the swollen appendage. As the appendage heals, the swelling reduces and, in some cases, the appendage actually shrinks to a size smaller than normal. Consequently, a gap is created between the appendage and the inner surface of the cast. To combat this widening gap, the pressure pouches/bladders 66, 67 may be inflated with fluid, thereby expanding the width of the wrap in the area of the inner surface of the cast and associated sensors and electrodes stay in contact with the user's skin.

Figure 5:
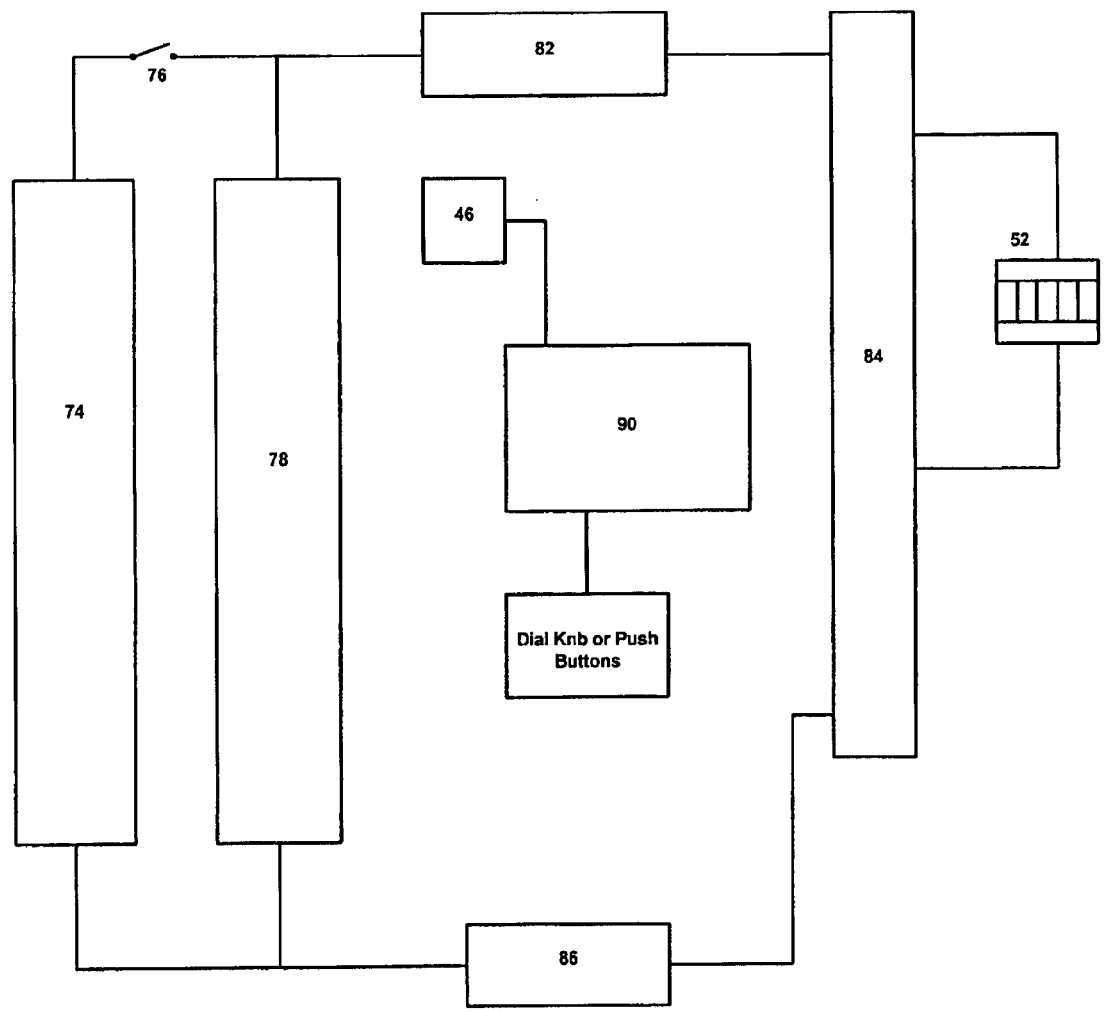
FIG. 5 is a block diagram of a circuit associated with a first embodiment of the invention.

FIG. 5 discloses a block diagram of a circuit device associated with a first embodiment of the therapeutic apparatus. The circuit device generally comprises a power unit 70 and a control unit 72. The control unit 72 communicates with the TE device 52 to operate the TE device 52 as one of a heater and a cooler, thereby delivering a desired temperature to the body surface of the user. The power unit 70 provides the necessary power to the therapeutic apparatus. The power unit 70 includes a power supply 74, such as several batteries or fuel cells and an on/off switch 76 for activating and deactivating the power source 74. The power unit 70 includes a voltage limiting circuit/device 78, in parallel with both the on/off switch 76 and the power source 74, to control the voltage delivered by the power source 74.

The control unit 72 generally includes a controller, here, a microprocessor 90; a first switch, here, a digital thermostat 82; and a second switch, here, a polarity switch 84. The microprocessor 90 controls the desired temperature to be delivered to the body surface. The microprocessor 90 preferably has a manually adjusted temperature input element, such as a dial knob or push buttons, which allows a user to select several temperatures to be delivered to the body surface of the user. The digital thermostat 82, which receives input from the temperature sensor 46, respond to the actual temperature detected by the temperature sensor 46 and disconnects the power unit 70 when the actual temperature is above a maximum temperature or below a minimum temperature. To do so, the digital thermostat 82 includes high temperature and low temperature safety switches. The high temperature safety switch limits the maximum temperature that the therapeutic apparatus can attain, and the low temperature safety switch limit the minimum temperature that the therapeutic apparatus can attain. The TE device 52 is connected to the control unit 72 to receive a signal from the microprocessor 90 corresponding to the desired temperature, and, in response to the desired temperature, delivers the desired temperature to the body surface.

A polarity switching circuit 84 communicates with the TE device 52 and switches the direction of current through the TE device 52 to operate the TE device 52 as a heater or a cooler. The polarity switching circuit 84 may comprise a simple switch that is operable by the user between hot and cold switch positions.

The control unit 72 also includes a current limiting device 86 connected to the power unit 70 and the second switch 84. The current limiting device 86, in its simplest form, a current limiting resistor and a low pass filter, limits the amount of current flowing through the TE device 52 to protect the TE device 52 from harmful power surge. The current limiting device 86 also prevents the TE device 52 from generating excessive temperature (heat or cold) that might harm the user by controlling the heating and cooling rate of the TE device 52.

During operation of the embodiment of FIG. 5, DC voltage from the power source 74 is applied to the digital thermostat 82. The output voltage from the digital thermostat 82 is applied to the polarity circuit/switch 84. The polarity circuit/switch 84 determines which direction the current will flow in the TE device 52. Where the polarity circuit/switch 84 comprises a switch, the user can activate this switch 84 to cause the TE device 52 to operate as either a heating device or a cooling device.

Figure 6:
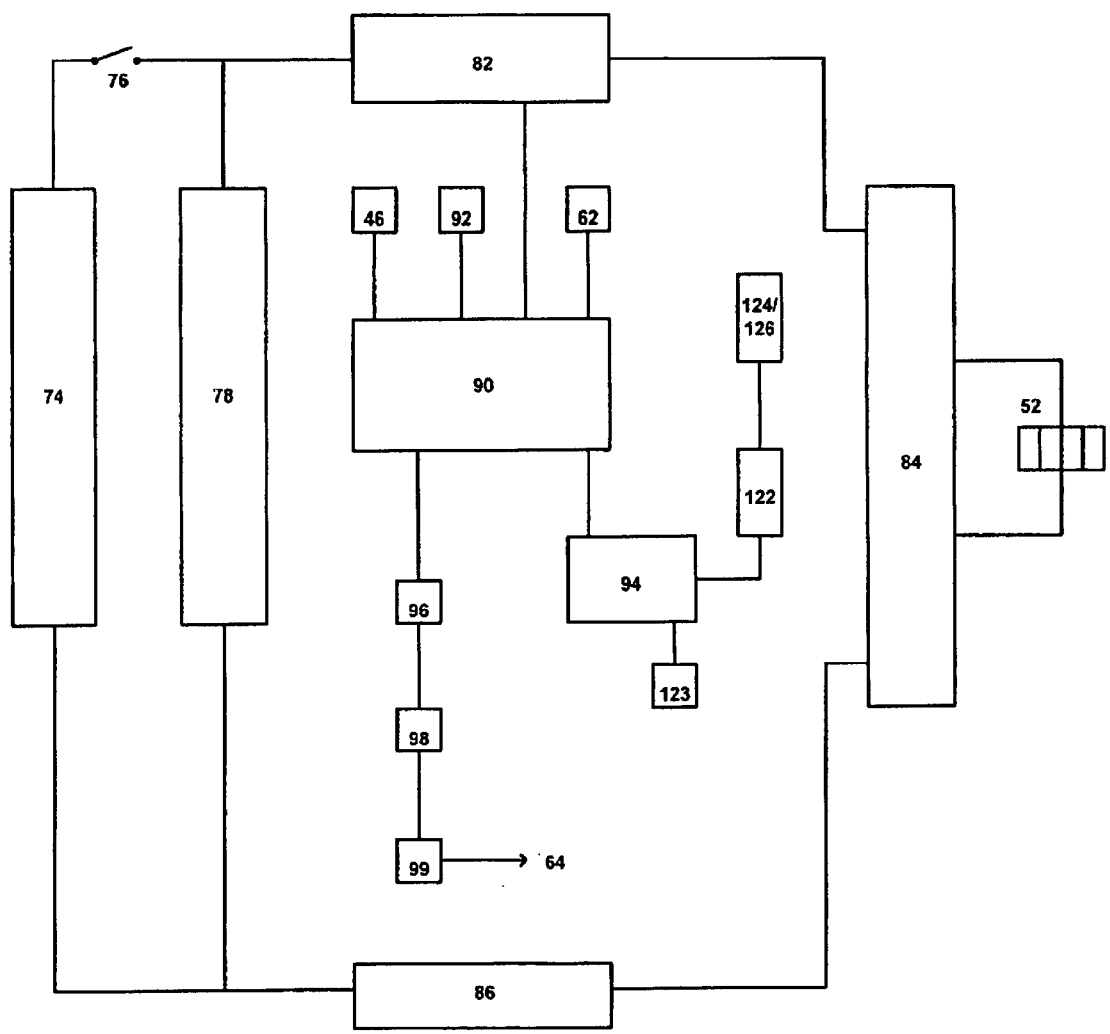
FIG. 6 is a block diagram of a circuit associated with a second embodiment of the invention.
Figure 7:
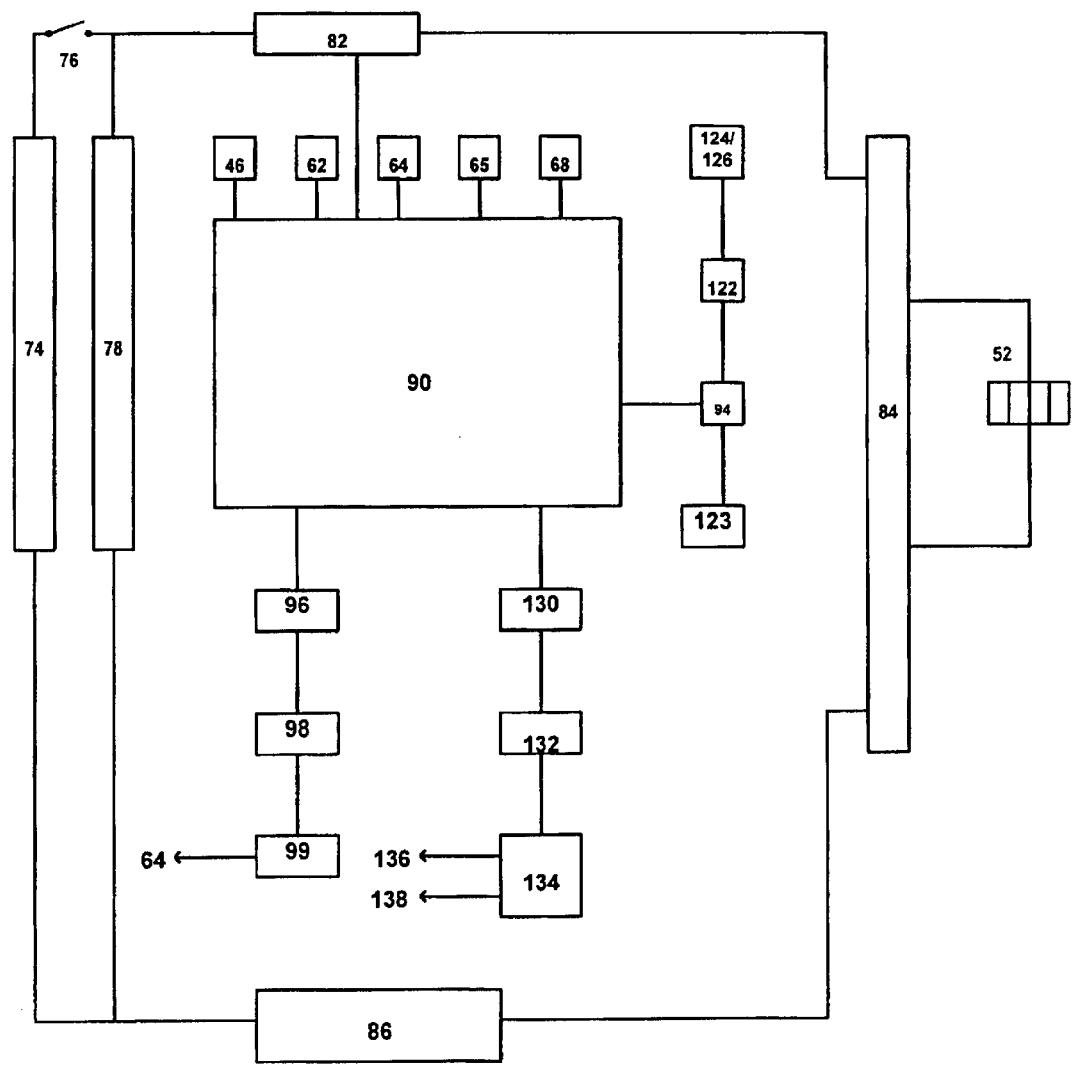
FIG. 7 is a block diagram of a circuit associated with a third embodiment of the invention.

FIGS. 6 and 7 are block diagrams of the second and third embodiments of the therapeutic apparatus, respectively. The control units 72', 72" of these embodiments employ a microprocessor 90 as the controller. Through input from the various sensors, the microprocessor 90 (1) determines if the wrap has been properly positioned on the user, (2) ensures that the proper temperature is maintained, (3) sets the length of treatment, (4) sets the duty cycle, (5) stores relevant data, (6) check for tampering of the apparatus and (7) ensures that the apparatus is not adversely affecting the user. As mentioned above, a pressure sensor 62 measures pressure for proper alignment. Motion, heart rate, breathing and pulse rate sensors 92, 93, 95, 97 can provided for monitoring user motion and user vital signs. Based on the user's motion and vital signs, the microprocessor program may modify the duty cycle of the treatment (i.e., the time that the apparatus is producing cooling or heating or electrical stimulation (active mode) versus the time that the apparatus is in a passive mode). The microprocessor 90 also can modify the thermal differential to be developed by the TE device 52, which in turn determines what temperature will be developed by the TE device 52, which in turn determines what temperature will be at the second conductive layer of the apparatus adjacent to the user's body surface.

The microprocessor 90 has memory in the form of a multi-section storage memory. The memory stores at least one program that dictates the desired temperature over a period of time based on a series of parameters. For example, one program may direct heat for 20 minutes and then cold for 20 minutes, alternating, over a period of 4 hours. The memory can also store a plurality of programs of different time and temperature parameters, where the programs are selectable via the input/output interface 94. The programs are preferably stored in secure memory. Alternately, the microprocessor 90 can be programmed by an external programming source to adjust the parameters by which the TE device 52 will operate. The external programming will come via a wired or wireless data link to some external-programming source such as a computer 501. These parameters include the operating temperature of the TE device 52 and the duration of treatment to the user. The memory also stores information recorded during operation of the TE device 52 in a second secure memory.

The input/output interface 94 allows a qualified practitioner to program the microprocessor for specific duty cycles and temperature. The programmable microprocessor 90 further includes tamper detection program(s) that detect if there is any unauthorized modification to the external sensors, programmable controller, other components within the controller, and/or power unit that might affect the proper functioning of the apparatus.

FIG. 6 shows also an embodiment of the apparatus that includes an electrical stimulation embedded unit to effect electrical stimulation. The electrical stimulation unit includes a waveform generator 96 electrically connected to a modulator 98, which is connected to a driver 99, then to electrodes 64. The microprocessor 90 controls the output of the waveform generator 96 in terms of signal amplitude, signal duration, signal polarity, and signal shape. For example, the microprocessor 90 can direct the modulator 98 to emit signals of controlled duration to provide pulsed electrical stimulation. The output of the modulator 98 is the driving function to the driver 99. The output of the driver 99 is applied to at least four electrodes 64, which are attached to the inner layer of the wrap (see, for example, FIG. 4e) and contact the user's skin. The use of electrical stimulation impulses to relief pain has been proven the use of Transcutaneous Electrical Nerve Stimulation (TENS), by Inferential Current Stimulation (ICS), and by Neuromuscular Electrical Stimulation (NMES). TENS and NMES require only two electrodes, while, ICS requires four electrodes to deliver biphasic pulses to the user's skin surface.

Figure 11:
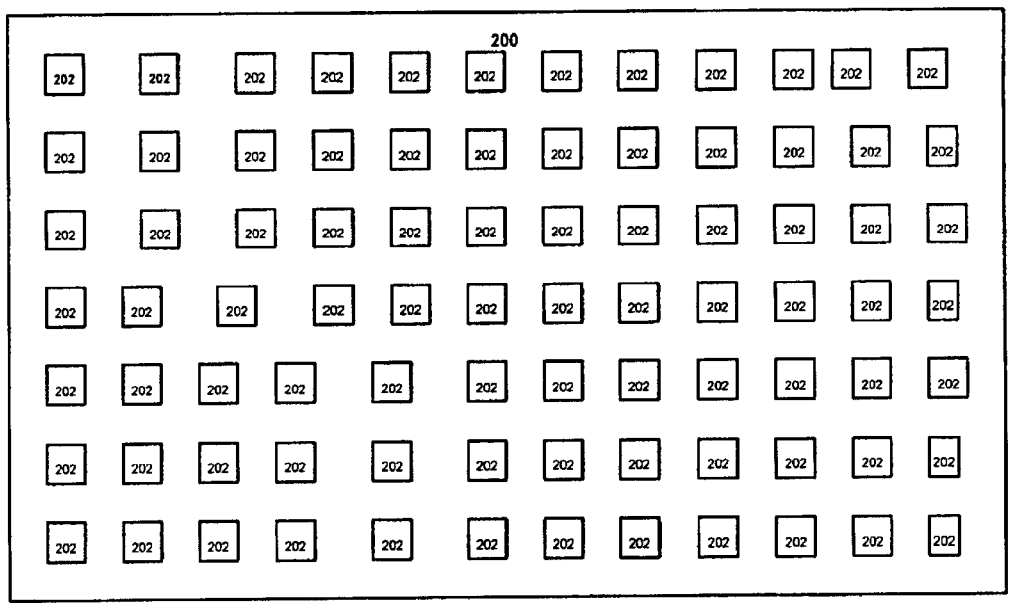
FIG. 11 is a schematic of a top view of the template for location of electrode(s) on the wrap.

In another embodiment, the locations of the electrodes are quite critical in the electrical stimulation provided to the user. Embedded in the inner layer 44 of the wrap 40 are at least two pouches 202 for each electrode 64 for positioning by the clinician to optimize the electrical stimulation effects for the specific area of treatment on the user's body surface. An overlay template 200 is used to determine which of the pouches 202 on the inner wrap 44 is used for a specific electrode 64. The overlay template 200 is placed on the user's body in the area of treatment. The clinician notes the pouch(s) 202 location(s) for optimal electrical stimulation therapy and then places the electrode(s) in the appropriate pouch location (as noted on the template) on the inner wrap 44. FIG. 11, shows the embodiment of the overlay template 200.

The electrical stimulation circuit enables a clinician to deliver electrical stimulation to the target area of the user's body. The electrical stimulation provides a safe, drug-free method of pain-relief, of muscle strengthening, and of treating soft tissue injuries. The electrical stimulation is delivered to the user via the microprocessor 90 programmed by the clinician. Because the microprocessor 90, as part of the electronics package, can be removed from the wrap, the microprocessor 90 may be programmed by the clinician at a remote computer 501. Typically, a modulated DC voltage at a frequency of up to 5,000 Hertz with a duty cycle of up to 15% is delivered to the user's body. This electric impulse stimulates muscle by stimulating a nerve(s) associated with the muscle or group of muscles. The electric impulse interrupts the transmission of pain through the nerve, providing an anesthetic effect, and then triggers the release of endorphins from the body as pain-killing chemicals. Selective treatment of the targeted body area with electrical stimulation, heating or cooling, or both, coupled with regular exercise, can provide the user with optimal clinical results. In this connection, a goal of the apparatus is to provide the most effective technology for rehabilitation programs aimed at improving the arms, trunk, legs, elbows, knees, shoulders, lower back and upper back strength of the user and the endurance of the user.

In another aspect of the apparatus, as shown in FIG. 7, the wrap includes an iontophoresis medication application element, which could be used along with the heating/cooling and electrical stimulation. The microprocessor 90 provides programmed medication to the user's body surface and sends output signal to the medication interface 130, which in turn signal the medication controller 132; the medication controller signals the medication dispenser 134 to send medication to the special electrode reservoir 138 and applies controlled potentials to the special electrodes 136, 138. The medication controller 134 controls the dosage, dose rate, duration and period of medication treatment.

Figure 8:
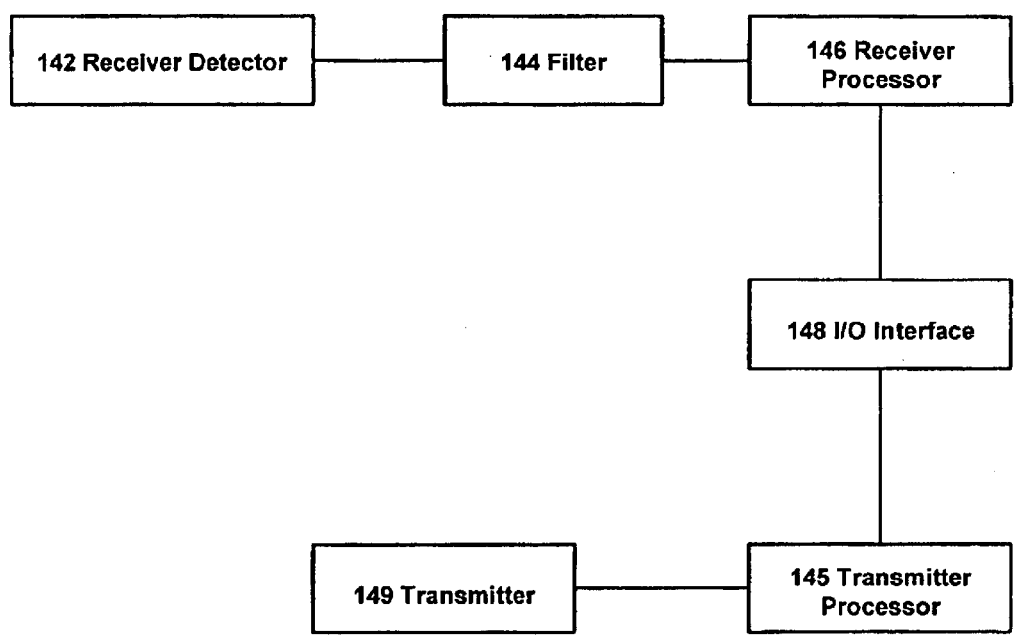
FIG. 8 is a block diagram of a wireless RF embodiment of the invention.
Figure 9:
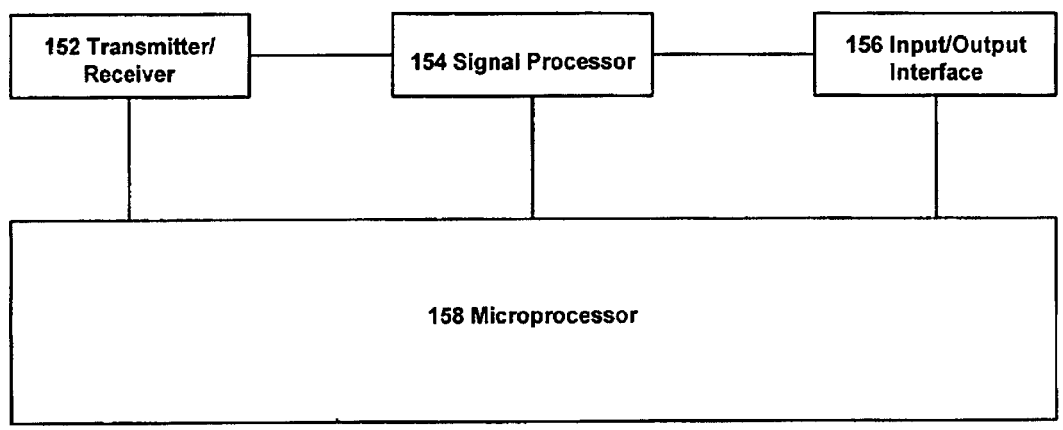
FIG. 9 is a block diagram of a wireless IR embodiment of the invention.

Another embodiment is that of a wireless data link embedded within the controller unit. FIGS. 8 and 9 show the two wireless data link methods. The wireless data link can either be of an Infrared (IR) type (FIG. 8) or and Radio Frequency (RF) type (FIG. 9). In either case, the microprocessor 90 is connected to an input/output interface 94. One output from the input/output interface 94 is connected to a data input/output processor 122, this in turn is connected to a IR transceiver 124 or a RF transceiver 126. The transceiver, either 124 or 126, transmits or receives data from a remote computer 501. Another output from the input/output interface 94 is connected to an input/output receptacle 123. Proper wiring can connect this input/output receptacle 123 directly to the remote computer 501.

As shown in FIG. 8, an IR transceiver 124 comprises of the following components: (1) Receiver which includes a light detector 142, (2) Filter 144, (3) Receiver processor 146, (4) Input/output interface 148, (5) Transmitter processor 141, and (6) Transmitter/Light source 143. The receiver light detector 142 detects light energy, then transfer these energy to the filter 144 where filtering technique is applied to remove undesired light spectrum energy, and the output is sent to the receiver processor 146 to be analyzed for a predetermined time period to detect presence of data and correct the data from any errors that might have been introduced during the transmission of the data. The processed data is sent to the input/output interface 148 for use by some other unit such as data processor 122 or by the remote computer 501. For the transmitter side, data is sent to the input/output interface 148, the output is transferred to the Transmitter Processor 145 and is put into data packets with error correction algorithms, the output activates the transmitter/light source 149.

As shown in FIG. 9, a RF transceiver 126 comprises of the following components: (1) Transmitter/Receiver 152, (2) Signal processor 154, (3) Input/output interface 156, and (4) Microprocessor 158. The transmitter/receiver 152 provides the modulation and demodulation of the RF signal waveform. It has multiple receiver channels and contains up/down converters, frequency synthesizers and detectors, modulators, and switching circuits; On the transmit side, the transmitter/receiver 152 accepts outgoing data messages from the signal processor 154, continuous phase modulates the digital information, up-converts the frequency to RF frequencies, performs frequency hopping, and provides RF power amplification for output to the Transceiver's antenna. On the receive side, the transmitter/receiver 152 accepts RF energy inputs, rejects signals not of interest, down-converts, dehops, amplifies, filters, phase detects, and digitizes the message for output to the signal processor 154. The signal processor performs preamble and message data processing, the data is analyzed for a predetermined time period to detect presence of data and correct the data from any errors that might have been introduced during the transmission of the data. The processed data is sent to the input/output interface 156 for use by some other unit such as data processor 122 or by the remote computer 501. The microprocessor 158 has a executable program that directs the functions of the RF transceiver 126. This program provides control of the RF transceiver 126, processing of data packets for reception and transmission, input/output of data from interface elements, system time, and built-in test and fault detection.

Figure 10:
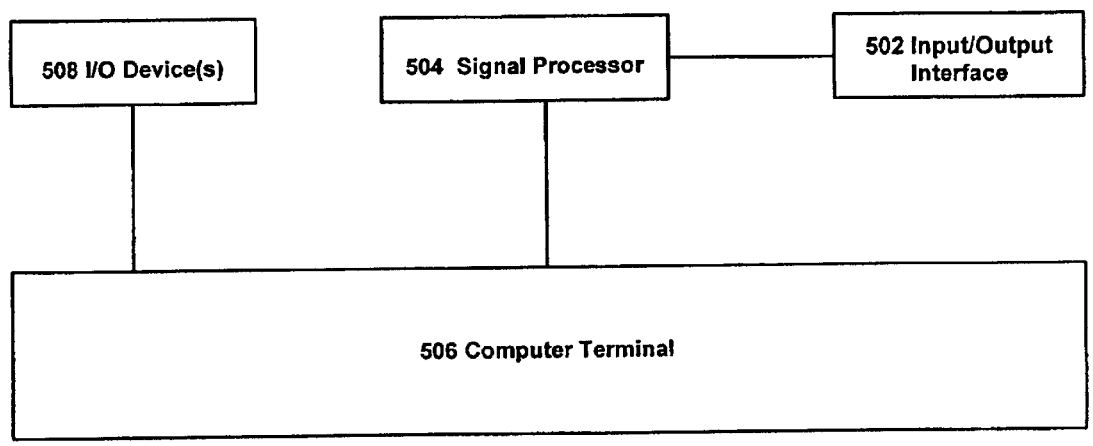
FIG. 10 is a block diagram of the remote computer embodiment of the invention.

As shown in FIG. 10, a further embodiment, is that of the remote computer 501. The remote computer 501 is the programming/controller for the apparatus. It programs the microprocessor 90 within the control unit 72. The remote computer 501 processes data from memory within the microprocessor 90, analyzes data, present data to the clinician, and reprogram the microprocessor 90 if so directed by the clinician. The remote computer 501 consists of input/output interface 502, processor 504, computer terminal 506, and input/output device 508.

The IR transceiver consists of the IR Receiver Detector Unit 142; Filter Unit 144; Receiver Signal Processor Unit 146; I/O Interface Unit 148; Transmitter Signal Processor Unit 145 and IR Transmitter Unit 149 as shown in FIG. 8.

Figure 12:
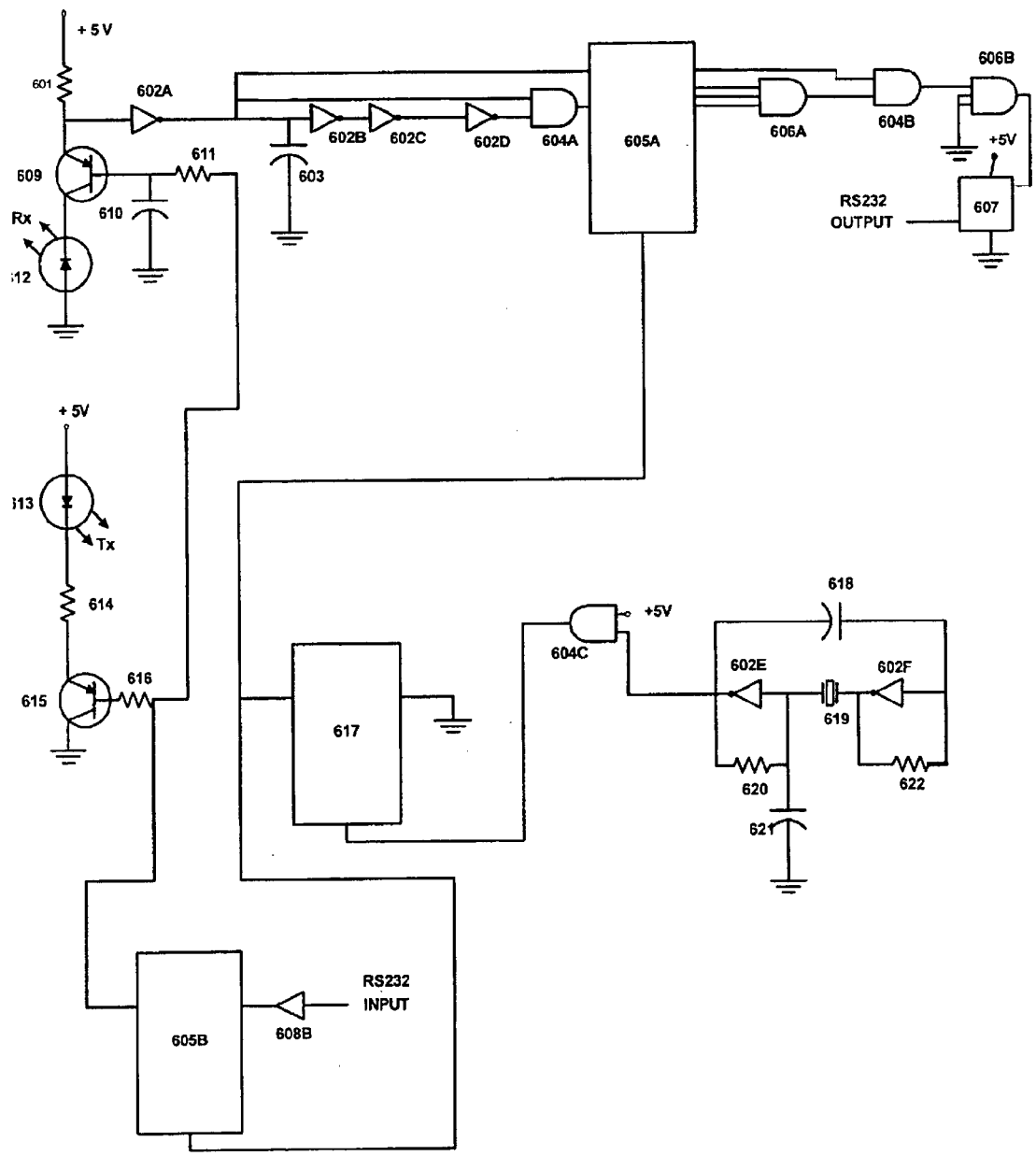
FIG. 12 is a schematic of the IR Transceiver embodiment of the invention.

As shown in FIG. 12, the IR Transceiver is composed of an IR transmitter unit 149 and an IR receiver unit 142. The IR format dictates half-duplex communications. Full duplex is not used due to the need to suppress reflections from the transmitter diode lamp 613. The module will enforce this by disabling the IR receiver while the IR transmitter is transmitting data. The IR transmitter and IR receiver runs on a 16X-clock source for the desired baud rate.

The IR transmitter unit 149 is quite simple. The following elements 602 E, 602 F, 618, 622, 620, 621 and 604 C form the crystal oscillator. Capacitor 621 is critical. The 2.4567 MHz crystal does not like to oscillate at its fundamental frequency. Capacitor 621 will suppress the overtones generated by the crystal oscillator. The binary counter 617 form the 16-X baud rate generator. The Transmitter Signal Processor 145 (UART) sends signals to the Inverter 608 B. The Inverter's 608 B output is combined with the output of the binary counter 617 in the 4-bit binary counter 605 B. The output of the 4-bit binary counter is connected with transistor 615, via resistor 616. The output of transistor 615 is connected to the IR diode lamp 613 via resistor 614.

When the IR transmitter is active (IR diode lamp 613 is on), the IR detector 612 is disabled by the 2N3906 609. For a short duration after the IR diode lamp 613 switches off, IR detector 612 will still saturated and it will require a recovery period. This recovery period is provided by capacitor 610 and resistor 611.

The IR receiver detector unit 142 uses 602 A, B, C, and D and capacitor 603 to shape the IR pulse going into the 4-bit binary counter 605 A (pin 4), and creates a reset pulse to synchronize the 4-bit counter 605 A. The outputs from the 4-bit binary counter are summed in the AND Gate 604 B. The output of AND Gate is connected to the Schmitt Trigger 606 B for signal conditioning. The output of Schmitt Trigger 606 B is connected to the D Flip-Flop 607. The output of the D Flip-Flop 607 is connected to an Inverter 608 A. The output of the Inverter 608 A is connected to the UART on the receive side. The UART is the Receiver Signal Processor Unit 146.

The Transceiver Signal Processor 146/145 modules will convert the signal from a Universal Asynchronous Receiver/Transmitter (UART) port into an infrared (IR) format, and back to UART format. It will handle baud rates of 9,600 baud. The IR format supports half-duplex communications only. The IR signal is compatible with a computer and other devices with an IRDA port.

The I/O interface units 148/156 (RS-232 port) is a Digital Terminal Equipment (DTE) port, which means it can be connected into a PC computer via a null modem cable or it connects to the I/O interface unit 94 within the electronics package 72.

Figure 13:
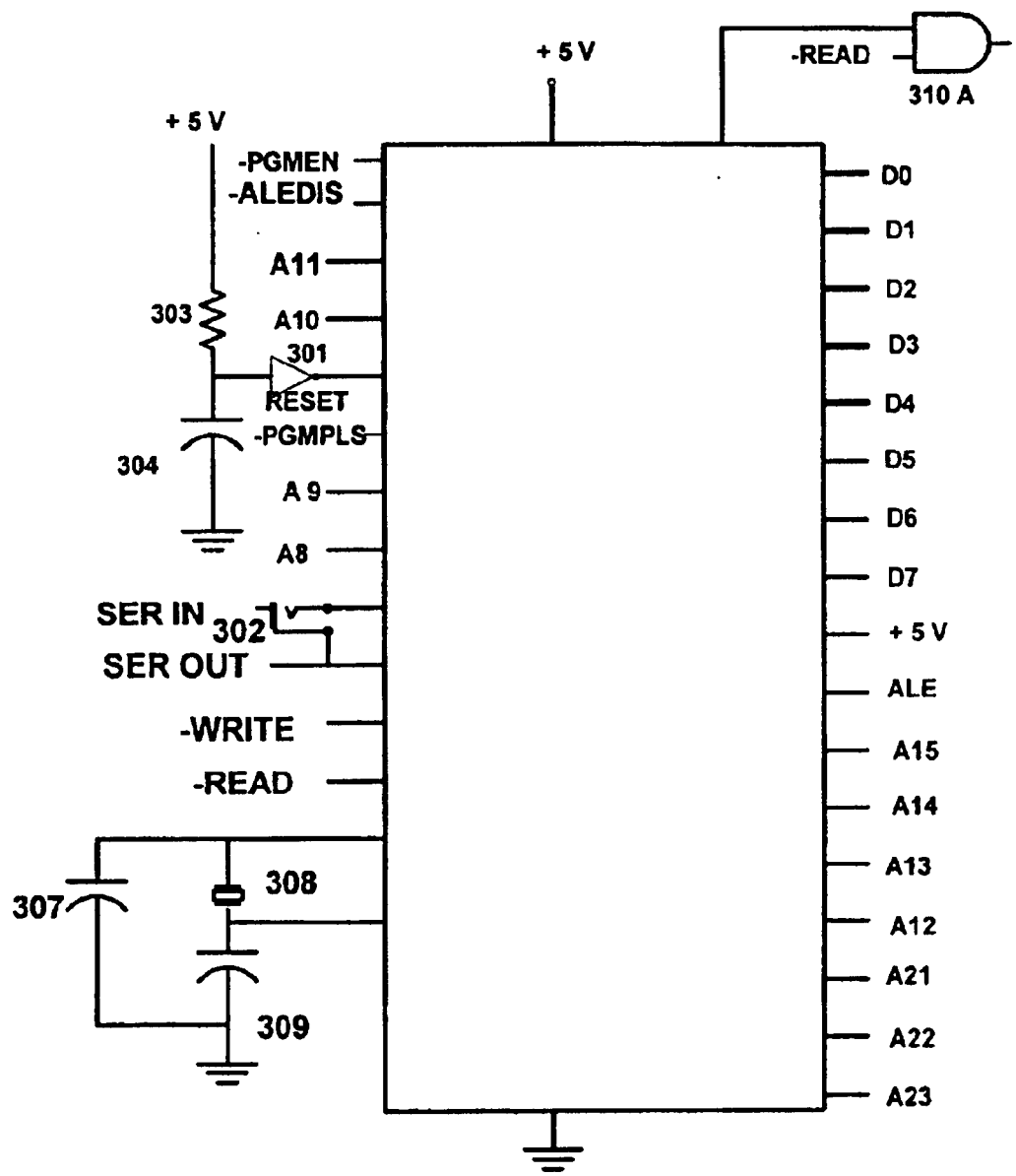
FIG. 13 is a schematic of the Microprocessor embodiment of the invention.
Figure 14:
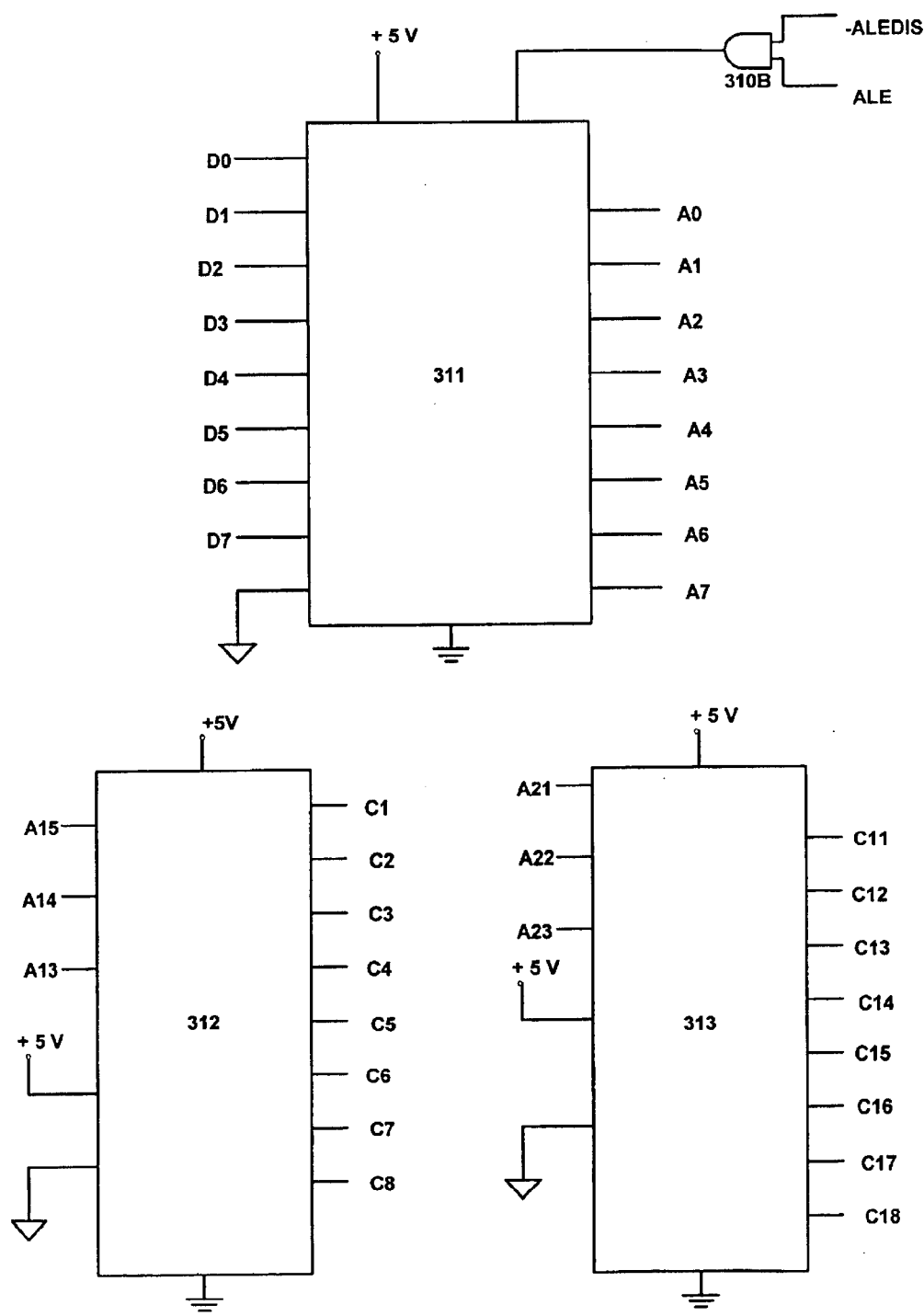
FIG. 14 is a schematic of the External Memory and Control Units embodiment of the invention.
Figure 15:
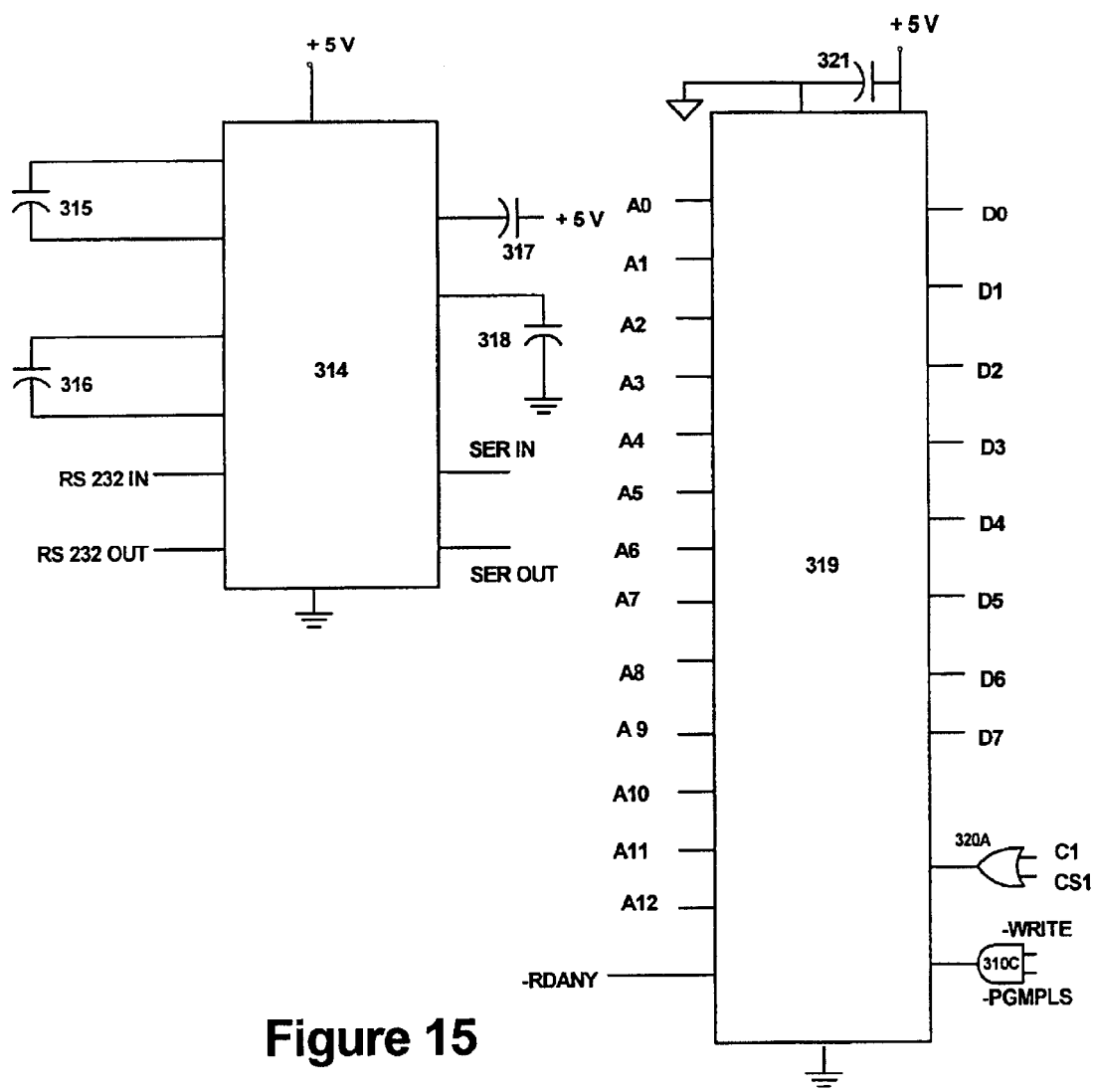
FIG. 15 is a schematic of the Internal I/O Interface Units embodiment of the invention.
Figure 16:
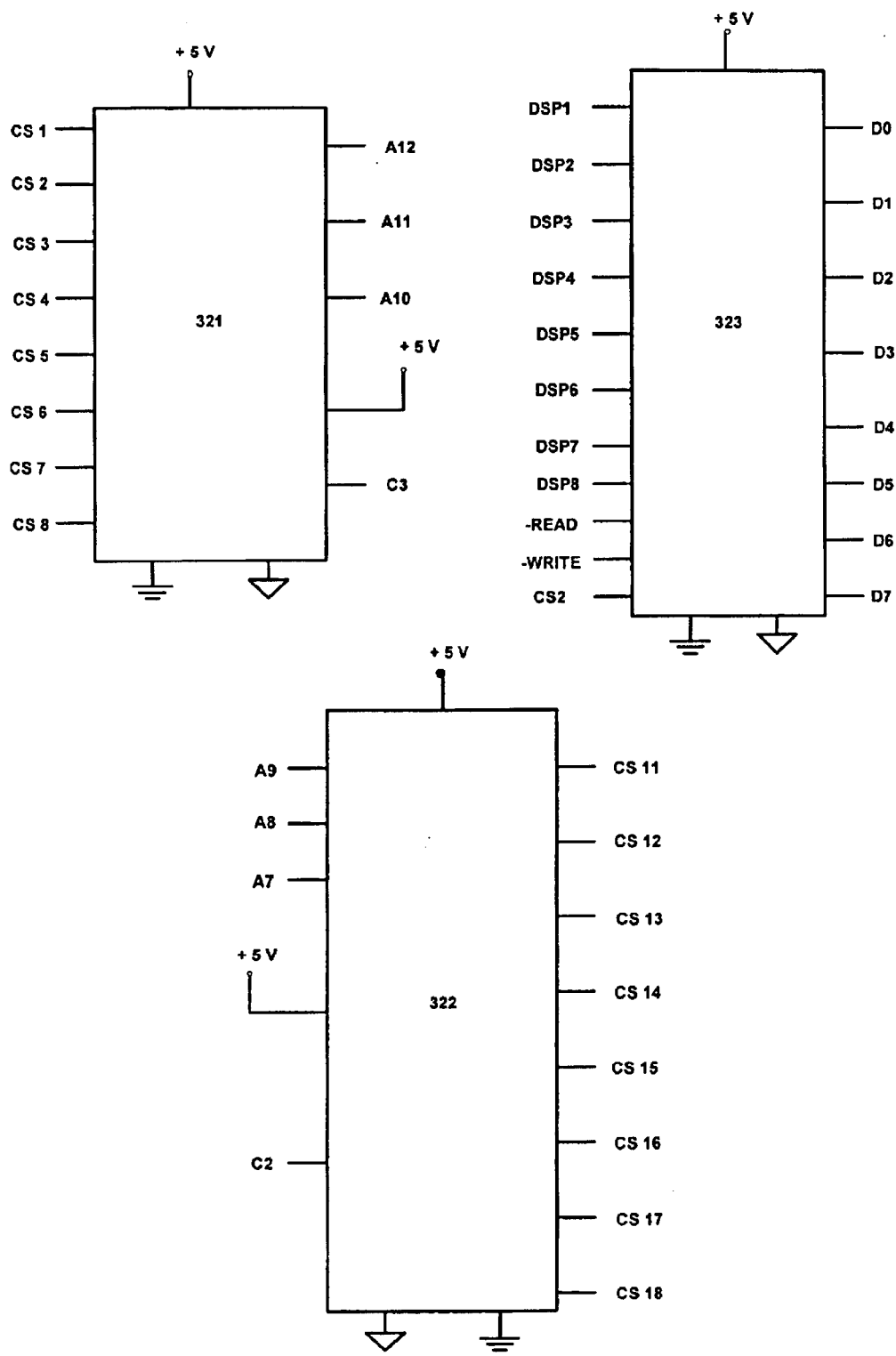
FIG. 16 is a schematic of the External I/O Interface Units I/O Interface Units embodiment of the invention.
Figure 17:
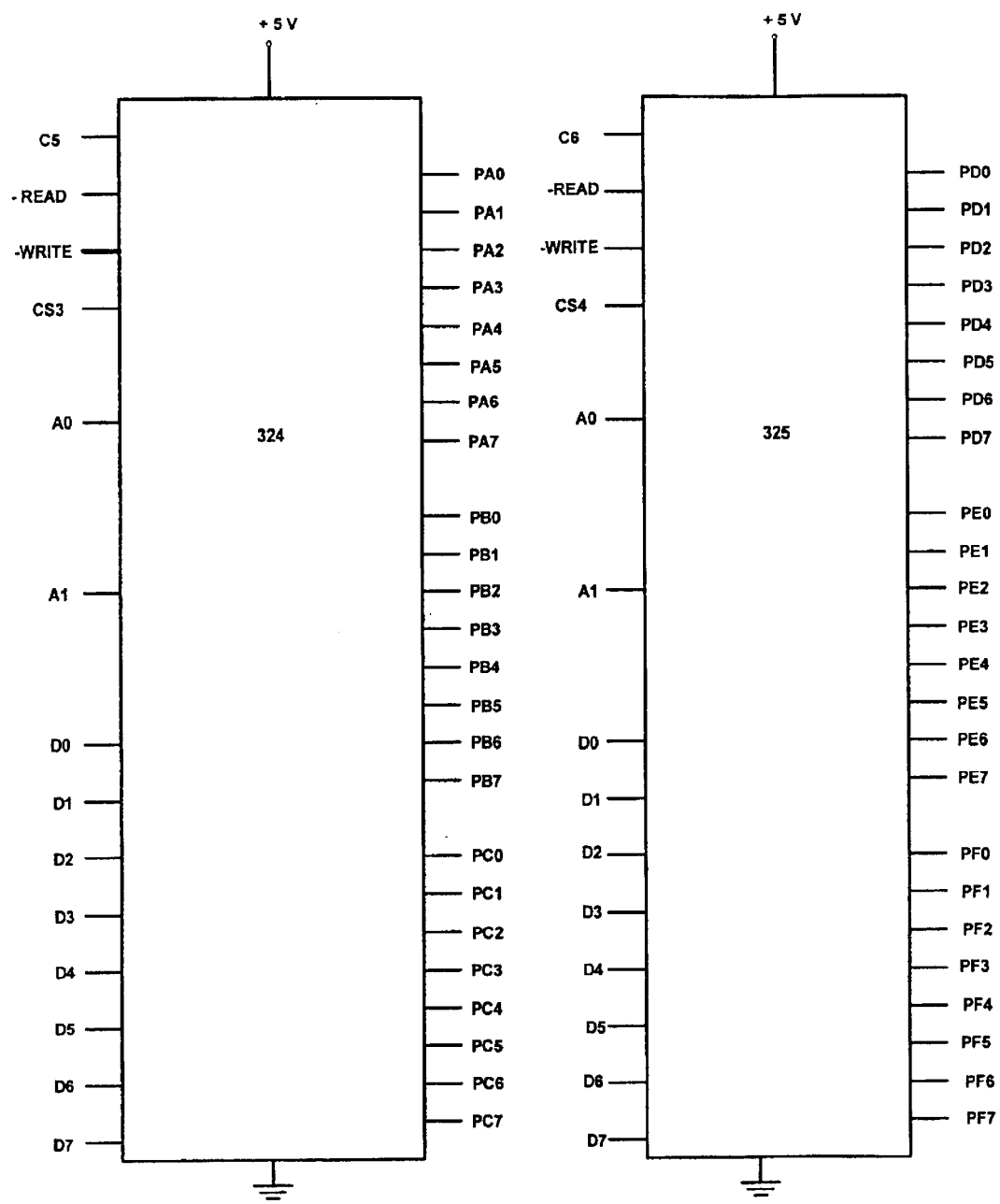
FIG. 17 is a schematic of the Parallel Output Interface I/O Interface Units embodiment of the invention.
Figure 18:
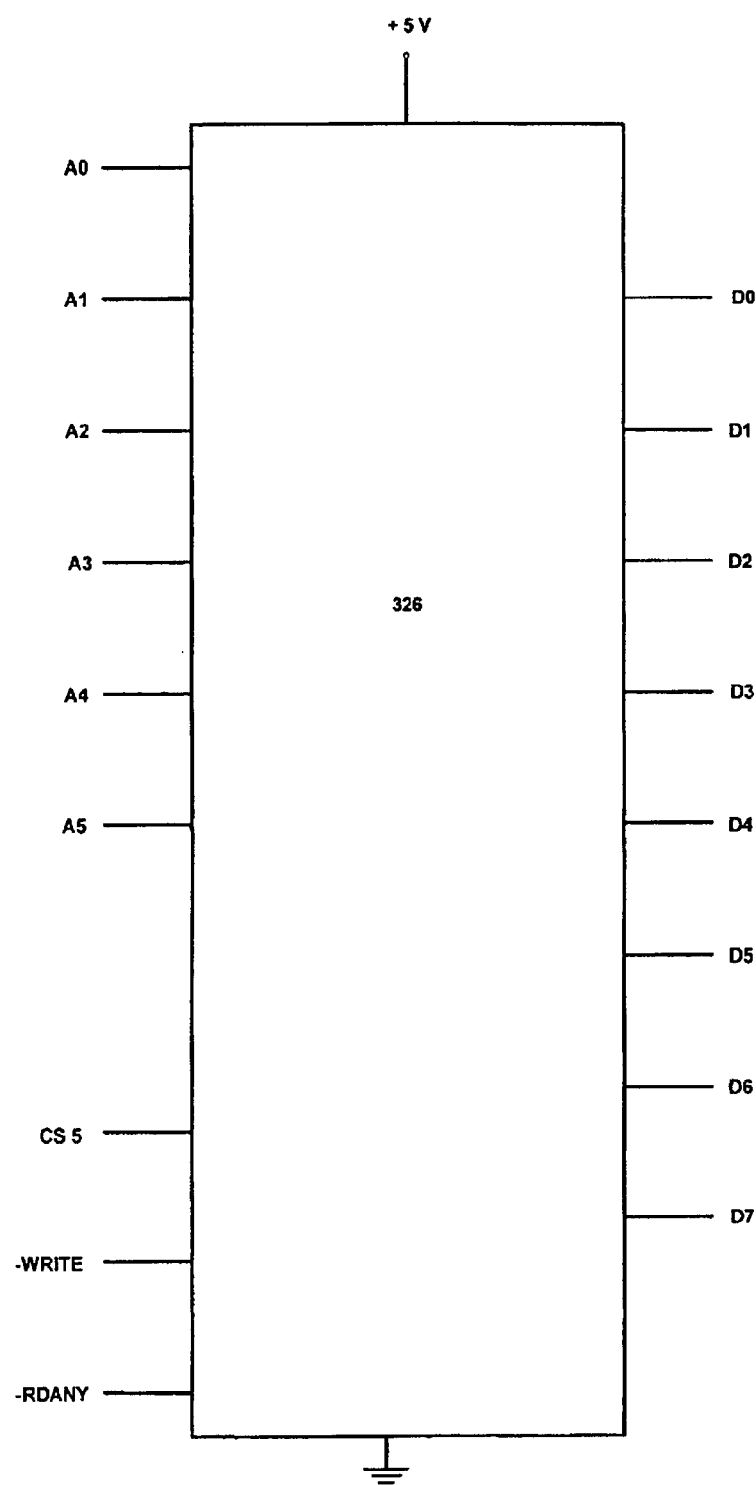
FIG. 18 is a schematic of the Watchdog Timekeeper embodiment of the invention.
Figure 19:
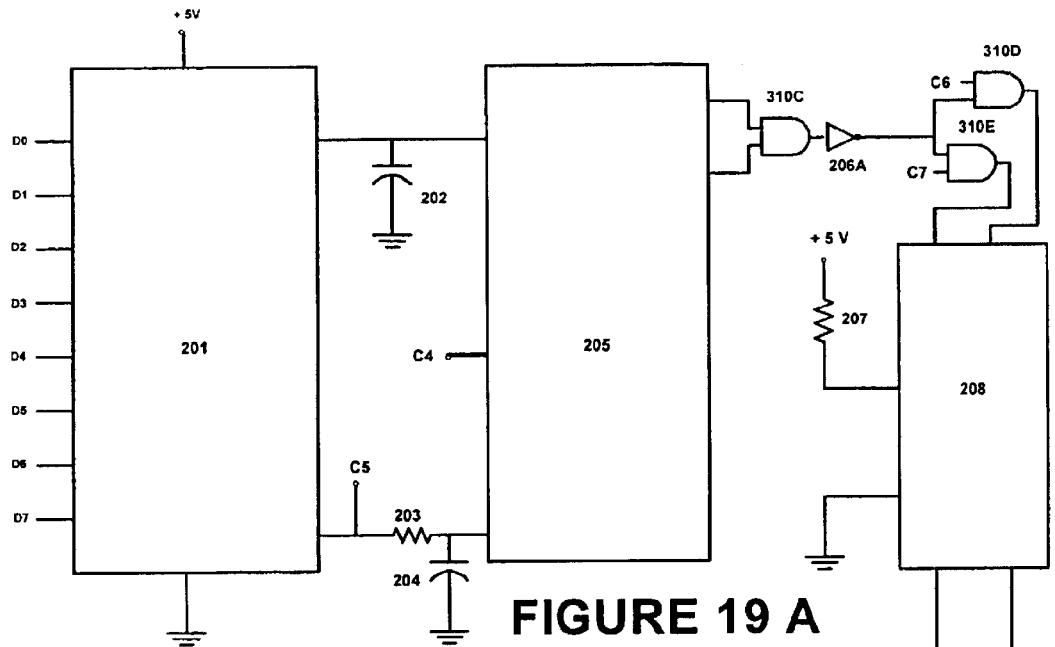
FIGS. 19A–C is a schematic of the Heating/Cooling embodiment of the invention.
Figure 19:
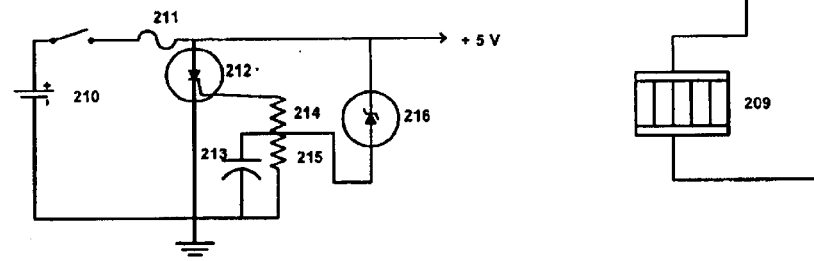
Figure 19:
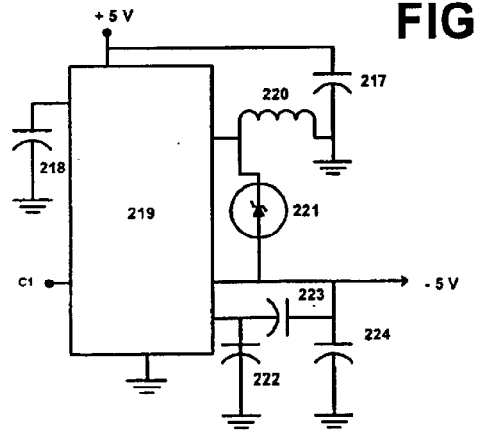

The microprocessor consists of the Microcontroller Unit 306, as shown in FIG. 13; External Static RAM Unit 313, Address Decoder Unit 312, and Address Latch Unit 311, as shown in FIG. 14; RS232 Interface Unit 314 and the Non Volatile RAM Unit 319, as shown in FIG. 15; Address Decoder Unit 321, Input Buffer Unit 323 and Output Latch Unit 322, as shown in FIG. 16; Parallel Output Units 324, 325 as shown in FIG. 17; and Watchdog Timer Unit 326 as shown in FIG. 18.

As shown in FIG. 13, the Microcontroller Unit is composed of a Microcontroller chip 306; resistor 303, capacitor 305 and inverter 301, which provides the reset function for the Microcontroller chip 306 each time the power is reapplied to the device; I/O Jack 302 allows for direct connection to an external computer without the need for the IR data link; Crystal 308, and capacitors 307, 309 determine the speed of the Microcontroller chip 306. AND gate 310A output provides the -RDANY signal.

As shown in FIG. 14, the Data outputs (D0 . . . D7) from Microcontroller chip 306 are connected to the (D0 . . . D7) of the Address Latch Unit 311 that stores the lower address byte during memory accesses. Because (D0 . . . D7) holds data to be read or written during memory access, the signals as a group are known as the Data Bus. The remaining Bus is the HIGH ADDRESS BUS (A8 . . . A15), which consists of the upper eight (8) address lines, and are not multiplexed. The Address Latch Unit 311 contains a set of D-type latches that store logic states. The Address Decoder Unit 312 is a 3-to-8 line decoder. It functions as the address decoder for the external memory. Address decoding allows multiple chips to connect to the address and data buses, with each chip enabled only when it is selected.

As shown in FIG. 15, a MAX232 driver/receiver 314, provides the RS-232 interface to the Microcontroller chip 306. Capacitors 315, 316, 317, & 318 provide suppression of undesired signals. Non Volatile RAM Unit 319 provides the storage of program instructions, look-up tables and various other data files. Capacitor 321 provides protection from any power surges that might affect the Non Volatile RAM Unit 319. OR gate 320A prevents the Non Volatile RAM Unit 319 from being accidentally overwritten during power-up. When the Microcontroller chip 306 first powers up, its port pins are in an unknown state for a brief period, until the reset algorithm in the chip brings them all high. During this time, there is a small chance that the right combination of outputs will cause a write operation to occur at Non Volatile RAM Unit 319 memory. Non Volatile RAM Unit 319 Select goes low only when reset is low and Microcontroller chip 306 is reading or writing to an address in Non Volatile RAM Unit 319. Output-enable connects to -RDANY, to allow Non Volatile RAM Unit 319 to be accessed as data or program memory. This enables Non Volatile RAM Unit 319 to store assembly-language routines as well as other programs. For writing to Non Volatile RAM Unit 319, AND gate 310C allows a choice of two control signals.-WRITE is the conventional signal for writing to data memory. In addition, Microcontroller chip 306 uses a special -PGMPLS signal to store other programs in Non Volatile RAM Unit 319 memory. Either of these signals will bring -WRITE low.

As shown in FIG. 16, Address Decoder Unit 321 is a 3-to-8-line decoder that generates individual chip-enable signals for blocks in the memory within the Non Volatile RAM Unit 319. The Address Decoder Unit 321 is enabled whenever the Address Decoder Unit 312 is low, which occurs when the Microcontroller chip 306 reads or writes to specified addresses. Address lines A10, A11, and A12 determine which of Address Decoder Unit's 321 outputs goes low when the chip is enabled. As with Address Decoder Unit 312, each output is low for a different memory area. A/D Converter 323 is used to interface eight analog inputs into the system. The connections are similar to those used by the Non Volatile RAM Unit 319. Digital outputs D0 . . . D7 are connected to DATA BUS. Output Latch 322 provides eight bits of output. The Output Latch Unit's 322 eight inputs are connected to the DATA BUS. Its output control is tied low so that the outputs are always enabled. NOR gate 320B clocks the Output Latch Unit 322 only when the Microcontroller chip 306 writes to specified addresses. When this occurs, the data written is latched to the outputs of Output Latch Unit 322. The outputs do not change until the next time the chip is written to. Output Latch Unit 322 is write-only.

Parallel Output Units 324, 325, as shown in FIG. 17, provide for numerous outputs to drive devices that require parallel data inputs. FIG. 17 shows Parallel Output Unit 324 accessed by control signal CS4 & Parallel Output Unit 325 accessed by control signal CS8. D0 . . . D7 connect to the system's DATA BUS, A0 and A1 connect to the lowest two address lines, and -READ and -WRITE inputs connect to the Microcontroller 306 matching outputs. RESET is connected the Microcontroller's RESET port. Six parallel I/O ports are available from Parallel Output Units 324 & 325 (PortA . . . PortF).

Shown in FIG. 18 is the Watchdog Timekeeper Module 326. The module is especially useful in a portable system, since it continues to keep time when the power supply is off. It is used to trigger different operations of the system at programmed times and intervals. After performing programmed operations, the invention is powered down until the next operation is required to be performed. At that time the module will signal the Microcontroller chip 306 to perform the next operation. The pinouts and wiring are similar to that of the Non Volatile RAM Unit 319. The module has two interrupt outputs.

The heating/cooling portion of the invention consists of the following components; Thermostat Unit 82, Thermal Electric Device 52 and Current Limiting Device 86, as shown in FIG. 6.

As shown in FIG. 19A, the Heating/Cooling function is comprised of a Parallel to Serial Shift Resister 201; Programmable Thermostat 205; Resistors 203, 207; Capacitors 202, 204; Logic Gates 310, 207; Switch 208; and a Thermal Electric Element 208. The Programmable Thermostat 205 determines the temperature range that the invention will operate within. The Programmable Thermostat 215 is a digitally controlled device, whose control is by communication by means of a 3-wire serial port interface. The output control of the thermostat is determined by parallel input signals D0 . . . D7, received by Parallel-In/Serial-Out, 8-bit Shift Register 201. The serial output is then connected to Programmable Thermostat 205. Control signals (C4 & C5) determine when the output switch signal of the programmable thermostat is adjusted. The output switch signals selection from the Programmable Thermostat Unit 205 is determined by the Microcontroller 306, and by control signals (C6 and C7). Combined by logic ANDs 310C, 310D, 310E and logic Invert 206A provide the control signal for H Switch 208 which determines when and in what direction the current flows through the Thermoelectric Element 209. Resistor 207 is the Current Limiting Device 86.

Power Unit 70 is shown in FIGS. 19B and 19C. As shown in FIG. 19B, Power Source 210 provides 6 volts of DC current. An overvoltage protection circuit is provided by the following components: Capacitor 213; Resistors 214, 215 Selenium Controlled Rectifier (SCR) 212; Zener Diode 216 and Fuse 211. The output is a regulated +5 volts DC. FIG. 19C is a simple inverter circuit with a negative voltage output. In this circuit, a MAX 735 219 current-mode pulse width modulated regulator provides with minimum external components a method of converting +5 volts DC to a negative output of −5 volts DC. A switching frequency of >150 kHz allows for small external components. The external components consist of the following: Capacitors 218, 217, 222, 223, 224, Inductor 220, and Zener Diode 221.

Figure 20:
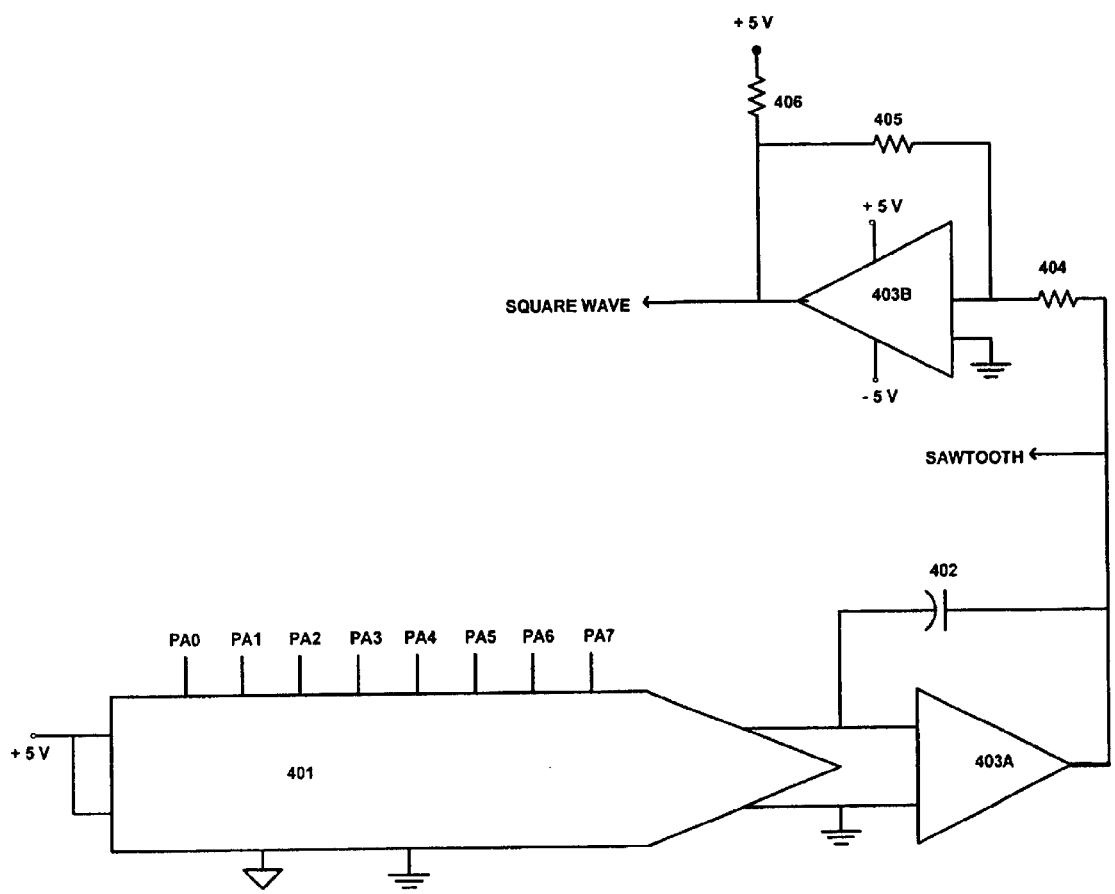
FIG. 20 is a schematic of the Waveform Generator for the Electrical Stimulation embodiment of the invention.
Figure 21:
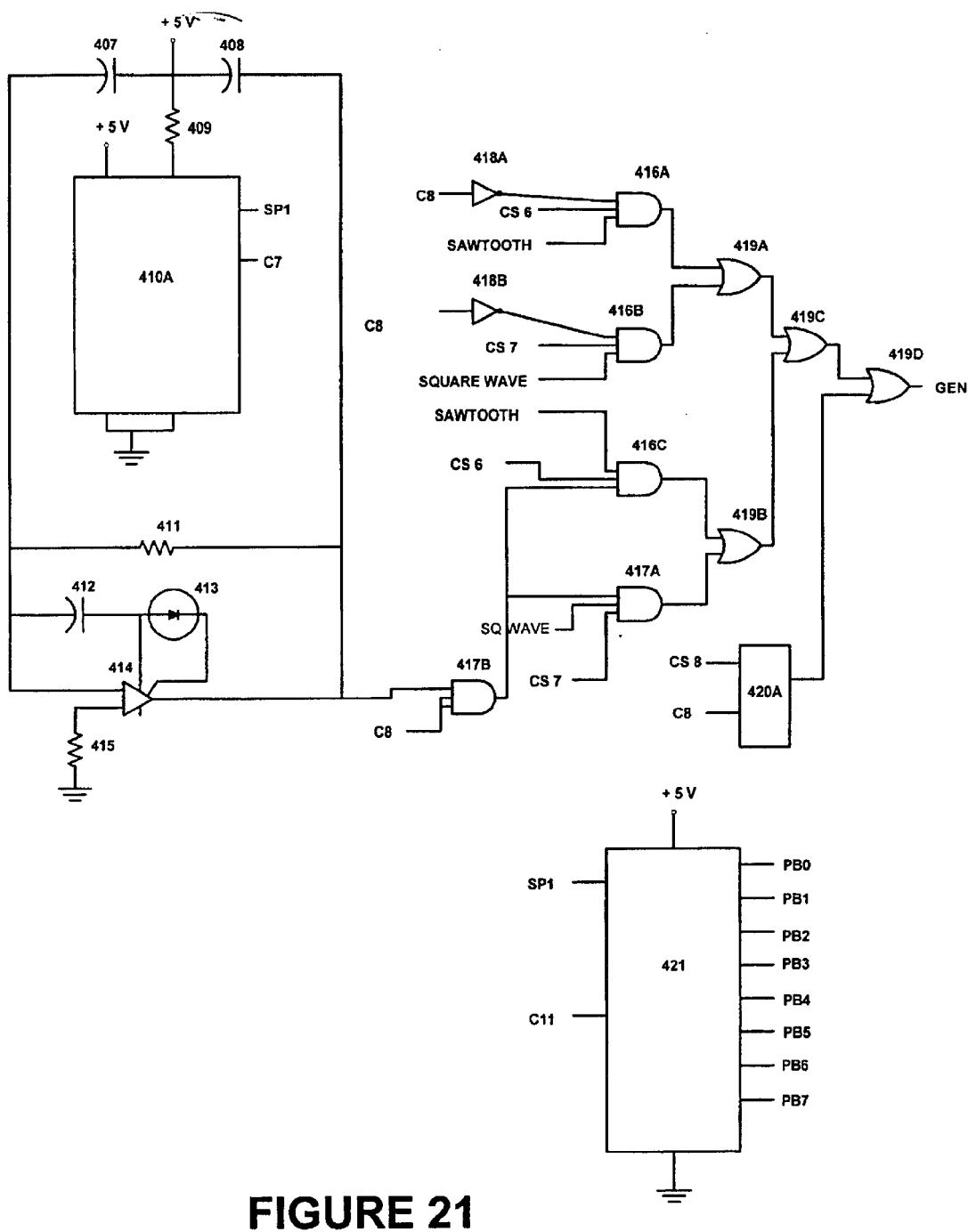
FIG. 21 is a schematic of the Modulator Unit for the Electrical Stimulation embodiment of the invention.

The electric stimulation portion of the invention consists of the Function Generator Unit 94, as shown in FIG. 20; Modulator Unit 98, as shown in FIG. 21; Driver Unit 99 as shown in FIG. 22; and Electrodes 64.

As shown in FIG. 20, the Function Generator Unit is composed of an 8-bit, D/A converter 401, capacitor 402 and OP Amp 403A, which provides the Sawtooth waveform for the Modulator Unit 98. Output from OP Amp 403A is connected to OP Amp 403B via resistor 404. Feedback resistor 405 is incorporated to ensure a square wave output from OP Amp 403B, resistor 406 provides correct bias for the square wave output signal As shown in FIG. 21, the Modulator Unit 98 is comprised of an oscillator section, consisting of a Programmable Potentiometer 410A, capacitors 407, 408 & 412, resistors 411 & 415, diode 413, and OP Amp 414; and waveform selection section consisting of logic ANDs 416 & 417, Inverters 418A & 418B and ORs 419A, 419B & 419C. The Programmable Potentiometer 410A determines the frequency response of the oscillator section. The Programmable Potentiometer 410A is a digitally controlled device, whose control is by communication by means of a 3-wire serial port interface. The ohmic value of the potentiometer is determined by parallel input signals PB0 . . . PB7, received by Parallel-In/Serial-Out, 8-bit Shift Register 420. The serial output (SP1) is then connected to Programmable Potentiometer 410A. Control signals (C11 & C7) determine when the ohmic valve of the programmable potentiometer is adjusted. The output waveform selection from the Modulator Unit 98 is determined by the Microcontroller 306, and by control signal (C4) and/or command signals (CS4 and/or CS5). Combined by logic ORs 419A, 419B, 419C provide the desired modulated waveform output (GEN).

It must be noted that all components in FIGS. 20 and 21 are not required if one would like to perform the same functions of these Figures by means of a nested software program within the Microcontroller Unit 306.

Figure 22:
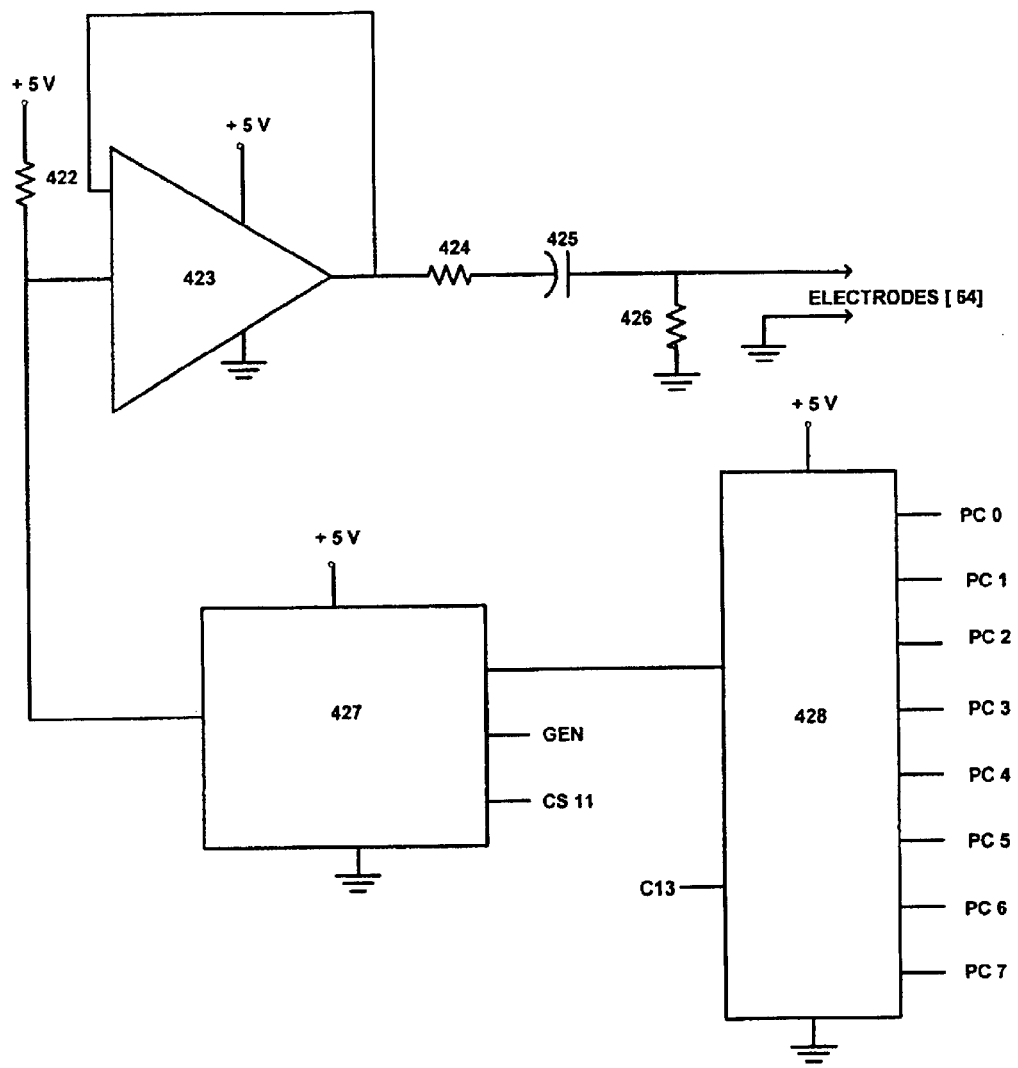
FIG. 22 is a schematic of the Driver Unit for the Electrical Stimulation embodiment of the invention.

As shown in FIG. 22, a Driver Unit 99, provides the necessary power density to the Electrodes 64 to provide electric stimulation to the invention user. The output waveform output can be either an unmodulated or a pulsed/modulated Sawtooth or Square wave or it can be a steady state waveform. The Driver unit 99 consists of the following components: Resistors 422, 424, 426, Amplifier 423, Capacitor 425, Programmable Potentiometer 427 and Digital to Analog Swift Register 428. The Programmable Potentiometer 427 determines the output current response of the driver section. The Programmable Potentiometer 427 is a digitally controlled device, whose control is by communication by means of a 3-wire serial port interface. The ohmic value of the potentiometer is determined by parallel input signals PC0 . . . PC7, received by Parallel-In/Serial-Out, 8-bit Shift Register 428. The serial output is then connected to Programmable Potentiometer 427. Control signals (C13) determine when the ohmic valve of the programmable potentiometer is adjusted. The output current from the Driver Unit 99 is determined by the Microcontroller 306, and by control signal (C12). The output current is connected to the Electrodes 64, which in turn is connected to the user's skin.

Figure 23:
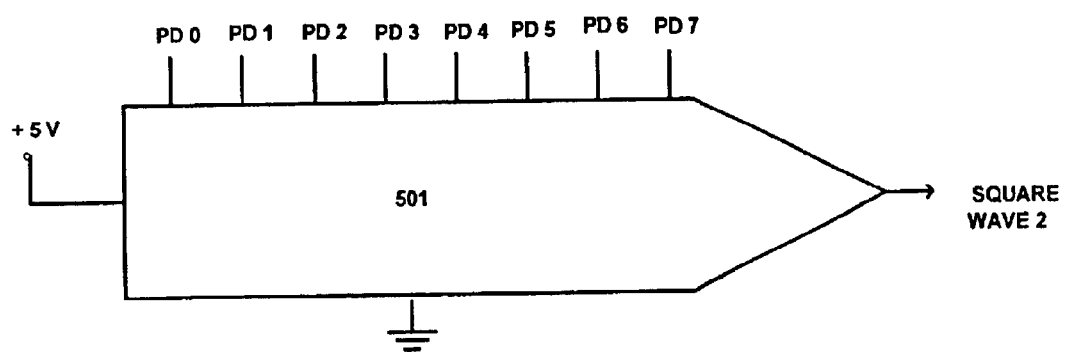
FIG. 23 is a schematic of the Medication Interface Unit for the Iontophoresis embodiment of the invention.
Figure 24:
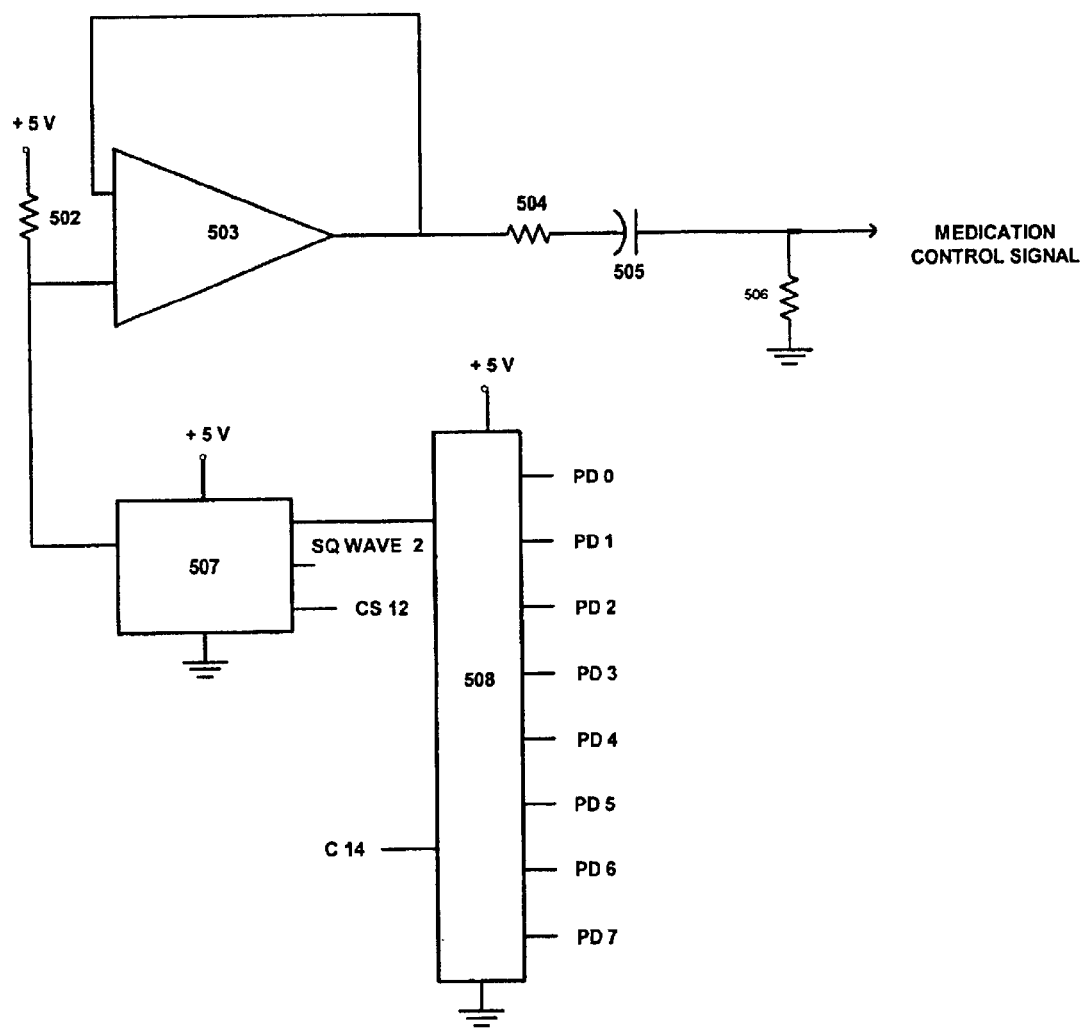
FIG. 24 is a schematic of the Medication Controller Unit for the Iontophoresis embodiment of the invention.

The iontophoresis portion of the invention consists of the Medication Interface Unit 130, as shown in FIG. 23; Medication Controller Unit 132, as shown in FIG. 24; Medication Dispenser Unit 134 as shown in FIG. 25; and Special Electrodes 136, 138.

As shown in FIG. 23, the Medication Interface Unit is composed of an 8-bit, D/A converter 501, controlled by Microcontroller 306 which generates a square wave output signal of proper amplitude, duration and duty cycle.

As shown in FIG. 24, a Medication Controller Unit 132, provides the necessary power density to the Electrodes 136, 138 to provide the proper potential to deliver medication to the invention user. The output waveform is either a pulsed Square wave or it can be a steady state waveform. The Medication Controller Unit 132 consists of the following components: Resistors 502, 504, 506, Amplifier 503, Capacitor 505, Programmable Potentiometer 507 and Parallel to Serial Shift Register 508. The Programmable Potentiometer 507 determines the output power density response of the medication controller section. The Programmable Potentiometer 507 is a digitally controlled device, whose control is by communication by means of a 3-wire serial port interface. The ohmic value of the potentiometer is determined by parallel input signals PD0 . . . PD7, received by Parallel-In/Serial-Out, 8-bit Shift Register 508. The serial output is then connected to Programmable Potentiometer 507. Control signals (C15) determine when the ohmic valve of the programmable potentiometer is adjusted. The output power density from the Medication Controller Unit 132 is determined by the Microcontroller 306, and by control signal (C14). The output current is connected to the Electrodes 136, 138, which in turn is connected to the user's skin.

Figure 25:
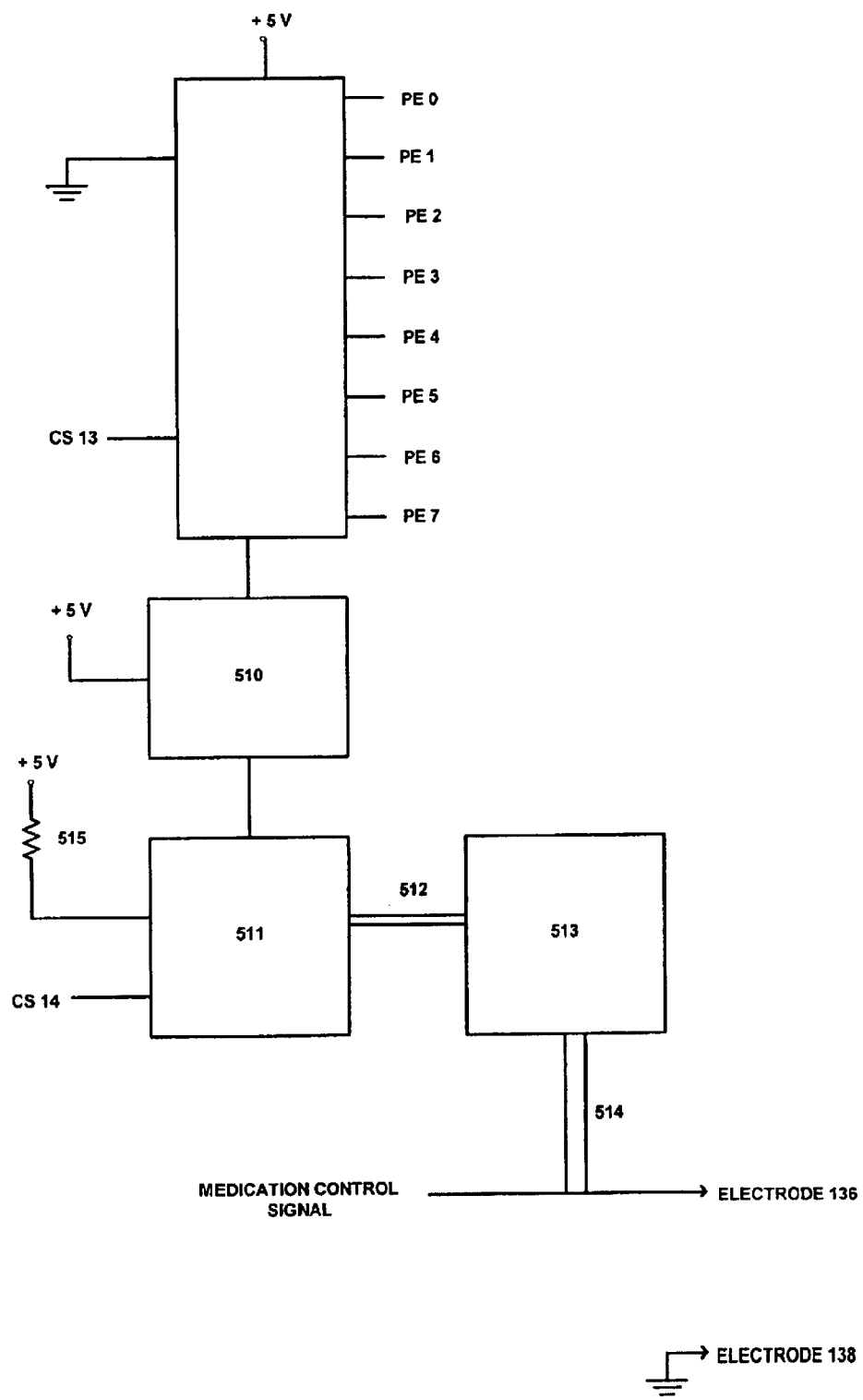
FIG. 25 is a schematic of the Medication Dispenser Unit for the Iontophoresis embodiment of the invention.
Figure 27:
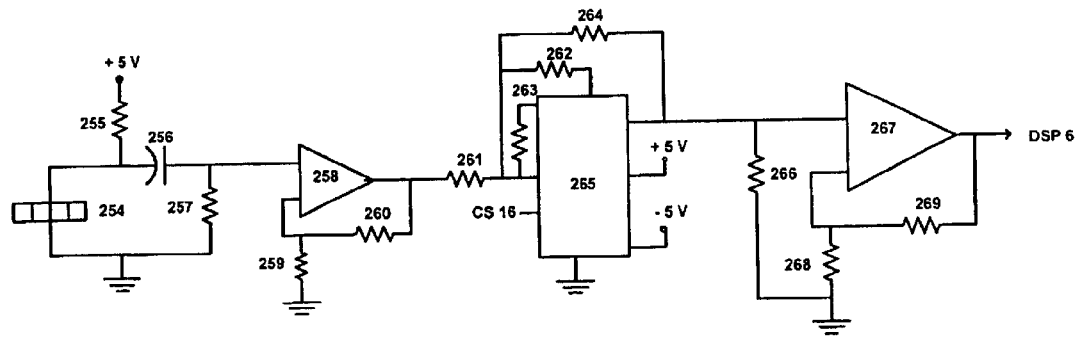
FIG. 27A is a schematic of the Heart Rate Sensor Unit for the Evaluation/Safety embodiment of the invention.
FIG. 27B is a schematic of the Breathing Rate Sensor Unit for the Evaluation/Safety embodiment of the invention.
Figure 27:
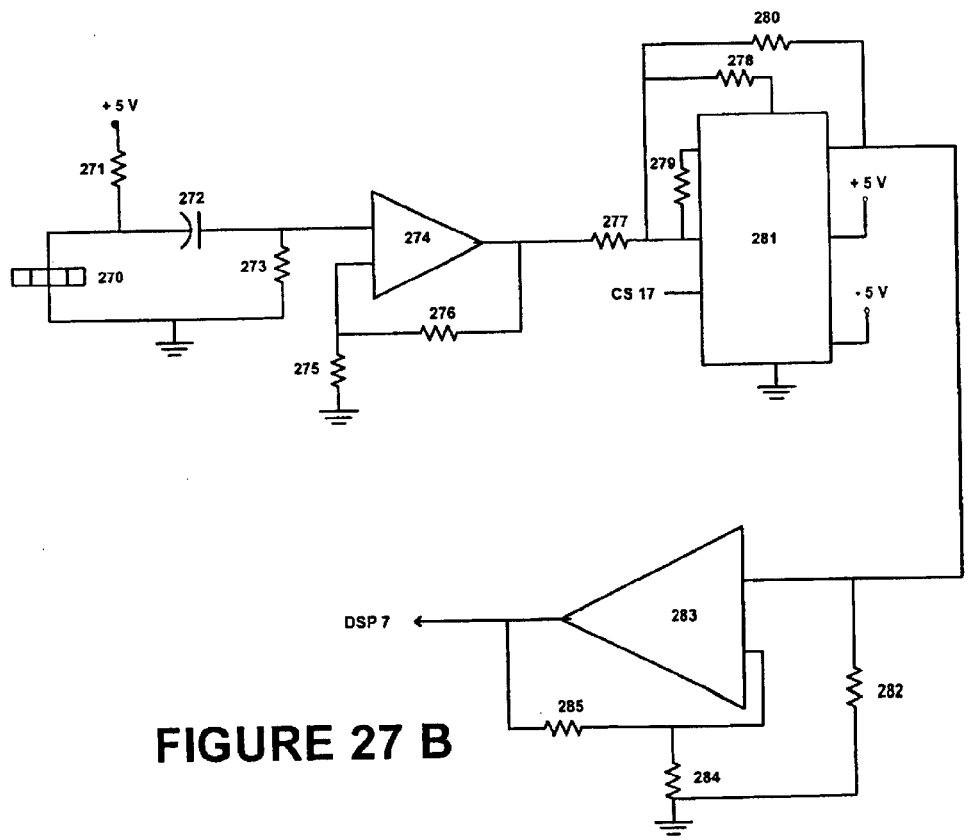

As shown in FIG. 25, a Medication Dispenser Unit 134 provides the necessary medication to the Special Electrode 136. The Medication Dispenser Unit 134 consists of the following components: Parallel to Serial Shift Register 509; Programmable Potentiometer 510; Micro Pump Unit 511; Shaft 512; Medication Reservoir Unit 513; and Tubing 514. The Programmable Potentiometer Unit 510 is a digitally controlled device, whose control is by communication by means of a 3-wire serial port interface. The voltage value of the potentiometer is determined by parallel input signals PE0 . . . PE7, received by Parallel-In/Serial-Out, 8-bit Shift Register 509. The serial output is then connected to Programmable Potentiometer Unit 510. Control signals (CS13 and PE0 . . . PE7) determine when the voltage valve of the programmable potentiometer device is adjusted. The output voltage from the Programmable Potentiometer Unit 510 is determined by the Microcontroller 306, and by control signal (CS13). The output voltage is connected to the Micro Pump Unit 511, which in turn turns Shaft 512, which is connected, to the Medication Reservoir Unit 513. The shaft rotation allows the internal pumping mechanism within the Medication Reservoir Unit 513 to sends the proper amount of medication to Special Electrode 136 via Tubing 514.

There are as many as five types of sensors that the invention has embedded within any wrap and can utilize any or all of these sensor outputs to accomplish the desired results. These include the following: 1) Temperature; 2) Pressure; 3) Evoked Responses; 4) Heart Rate; and 5) Breathing Rate.

As shown in FIG. 26A, the temperature sensor consists of a Resistor 225 and a Thermistor 226. As the temperature of the skin increases the ohmic value of the thermistor decreases exponentially and in the reverse as the skin temperature decreases the ohmic value of the thermistor increases. With the change of the ohmic value of the thermistor the output voltage at the junction of Resistor 225 and Thermistor 226 will vary with increase/decrease of the user's body temperature. Because of the accurate and repeatability of the resistance versus temperature characteristic of the thermistor an appropriate lookup table in conjunction with a microprocessor can eliminate the potential nonlinearity problem. This voltage is sent to DSP 1 for conversion to a digital value, which the microcontroller will use to adjust the thermostat outputs to provide the desired temperature from the thermoelectric device.

As shown in FIG. 26B, the pressure sensor consists of a piezoelectric acoustic speaker 227, OP Amp 228, and resistor 229. If one were to operate a piezoelectric acoustic speaker in a reverse mode, a voltage would be generated when pressure was applied to the speaker diaphragm. Piezoresistive materials have the unique ability to convert mechanical energy into electrical energy. This voltage will be amplified by OPAmp and then sent to DSP 2 for conversion to a digital value, which the microcontroller will use to determine if the proper pressure is applied to the wrap or location of the wrap is in the correct alignment.

As shown in FIG. 26C, the evoked response sensor consists of a low noise, Electret Condenser Microphone 230, capacitor 232, low noise preamp 234, and resistors 233, 235, 236. The desired signal along with background noise is detected by the microphone and is amplified by preamp. The output of the preamp is signal Vo1.

As shown in FIG. 26D, an active filtering stage that consists of a high performance, Switched-Capacitor Filter 241, and resistors 237, 238, 239, 240. An active filter use amplifying devices along with resistors and capacitors in their feedback loops to synthesize desired filtering characteristics. In the switched-capacitor filter require no capacitors in their operation. The center frequency (fo) of the filter is determined by the value of the control signal (CS 15). The Q of the filter is equal to the fo/BW or resistor 240/resistor 238. The low-pass gain of the filter is equal to —resistor 238/resistor 237 and the bandpass gain is equal to —resistor 240/resistor 237. The input signal Vo1 is connected to the Switched-Capacitor filter 241, four external resistors 237, 238, 239, 240 are connected to the filter to provide the following outputs: 1) low-pass (Vo2 A); 2) high-pass (Vo2 B); and 3) bandpass (Vo2 C).

As shown in FIG. 26E, the amplifier stage for the low-pass signal (Vo2 A) consists of an Op Amp 243 and resistors 242, 244, 245. The low-pass signal is amplified by OP Amp. This output signal is sent to DSP 3 for conversion to a digital value, which the microcontroller will use to either store or transferred, by the wireless link for real-time processing.

As shown in FIG. 26F, the amplifier stage for the high-pass signal (Vo2 B) consists of an Op Amp 247 and resistors 246, 248, 249. The high-pass signal is amplified by OP Amp. This output signal is sent to DSP 4 for conversion to a digital value, which the microcontroller will use to either store or transferred, by the wireless link for real-time processing.

As shown in FIG. 26G, the amplifier stage for the band-pass signal (Vo2 C) consists of an Op Amp 251 and resistors 250, 252, 253. The band-pass signal is amplified by OP Amp. This output signal is sent to DSP 5 for conversion to a digital value, which the microcontroller will use to either store or transferred, by the wireless link for real-time processing.

As shown in FIG. 27A, the heart rate sensor consists of a low noise, Electret Condenser Microphone 254, capacitor 256, low noise preamp 258, and resistors 257, 259, 260. The desired signal along with background noise is detected by the microphone and is amplified by preamp. The output of the preamp is sent to an active filtering stage that consists of a high performance, Switched-Capacitor Filter 265, and resistors 261, 262, 263, 264. The center frequency (fo) of the filter is determined by the value of the control signal (CS 16). The Q of the filter is equal to the fo/BW or resistor 264/resistor 262. The bandpass gain is equal to —resistor 264/resistor 261. The band-pass signal is sent to the amplifier stage. The amplifier stage consists of an Op Amp 267 and resistors 266, 268, 269. The band-pass signal is amplified by OP Amp. This output signal is sent to DSP 6 for conversion to a digital value, which the microcontroller will use to either store or transferred, by the wireless link for real-time processing.

As shown in FIG. 27B, the breathing rate sensor consists of a low noise, Electret Condenser Microphone 270, capacitor 272, low noise preamp 274, and resistors 273, 275, 276. The desired signal along with background noise is detected by the microphone and is amplified by preamp. The output of the preamp is sent to an active filtering stage that consists of a high performance, Switched-Capacitor Filter 281, and resistors 277, 278, 279, 280. The center frequency (fo) of the filter is determined by the value of the control signal (CS 17). The Q of the filter is equal to the fo/BW or resistor 280/resistor 278. The bandpass gain is equal to —resistor 280/resistor 277. The band-pass signal is sent to the amplifier stage. The amplifier stage consists of an Op Amp 283 and resistors 282, 284, 285. The band-pass signal is amplified by OP Amp. This output signal is sent to DSP 7 for conversion to a digital value, which the microcontroller will use to either store or transferred, by the wireless link for real-time processing.

The present invention recognizes several advantages. The present invention offers a technique for providing cooling or heating a targeted area of the user's body. For example, the apparatus of the present invention is suitable as a non-invasive analgesic for relief of headaches by providing controlled heating and cooling to a user's head. The present invention can be programmed by a medical clinician, licensed trainer, or licensed therapist to heat and cool to a specific temperature and for a specific duration. In addition, in the embodiment of FIG. 7, the electrical stimulation feature provides safe, drug-free method for providing relief from pain and for providing muscle strengthening, supplementing the therapeutic features of heating or cooling. Electrical stimulation also increases the recovery rate of soft tissue injuries. Further, the apparatus serves as a thermal therapeutic device in a protocol for treatment of invasive and non-invasive muscle and skeletal trauma.

Further, the present invention enables data acquisition so that information relating to when and how user used the present invention may be read-out and analyzed. The present invention includes a portable power source, such as a battery or fuel cell, to provide mobility to the user. Also, the present invention can be incorporated within a cast, if necessary.

The present invention also can be incorporated into clothing, either outer clothing or under garments, to provide controlled cooling or heating clothing. Because the apparatus may be mounted over clothing, the apparatus is ideal for motorcyclists, farmers, ranchers, construction workers, other outdoor tradesmen, outdoor enthusiasts, military personnel, merchantmen, and other professionals with outdoor job responsibilities. When mounted in an under garment, the apparatus can provide adequate cooling to personnel who work in extreme temperature environments, such as fire fighters or miners. The apparatus can be integrated in each clothing item, and each clothing item can be worn separately or in combination with other items to suit the user.

In addition to the heating/cooling and electrical stimulation aspects of the apparatus, some embodiments of the apparatus can monitor a user's body vital signs, such as temperature, heart rate, breathing rate, blood pressure and motion, and can indicate if the apparatus is correctly positioned on the user. Some embodiments can record the user's vital signs, activity, and apparatus use. In addition, the apparatus can monitor the battery and/or fuel cell discharge rate and can indicate when the power unit requires charging or replacement.

An evoked potential can be generated by deliberate stimulation of peripheral sense organs or their sensory nerves at any point along the sensory pathway. Evoked potentials differ from the spontaneous electrical activity that is transmitted within the nervous systems of both humans and animals in that they have a definite relationship to the onset of the stimulus and a constant pattern of response in relation to the neural structures being activated. This noninvasive technique allows for determination of functional status of major nerve circuits in the central nervous system.

When a cell is excited, it generates an action potential, ionic current begins to flow. In the case of a nerve cell with a long axon, the action potential is generated over a very small segment of its length. As the action potential travels along the nerve fiber, it cannot reexcite the portion of the fiber immediately behind the advancing wave of depolarization because of the refractory period that follows the action potential. However, excitation of a nerve fiber somewhere along its length can produce an action potential propagated in both directions from the original point of excitation. The rate at which an action potential moves along a nerve fiber or is propagated from cell to cell is called the propagation rate. In nerve fibers, this is known as nerve conduction velocity. This velocity varies widely, depending on the type and diameter of the nerve fiber.

The basic elements of this technique include the electrodes for detecting electrical activity in the nervous system, the preamplifier stage that amplifies the signal, conditioning stage that filters the signal to reduce the amount of background interference, additional amplifier to increase the amplitude of the biologic signal of interest, digitizing and processing stages to average multiple responses, control and memory stage to capture and store the evoked response.

The apparatus of the present invention may be modified for use by the equestrian community for treatment of equines for certain medical conditions. The apparatus may be mounted to an applique, designed for application to a horse, to provide programmable heating or cooling and/or electrical stimulation for extended periods of time so that the horse can stay mobile without any external connections or assistance. In addition, the apparatus can be modified for use by other animals for certain medical conditions.

As stated above, the apparatus can provide therapeutic treatment and/or evaluation of medical conditions, heating/cooling, electrical stimulation, drug administration, and monitoring in either real-time or recorded mode. The apparatus also can perform analysis in either real-time or another predetermined time frame. The apparatus can be constructed in a manner particularly suited for equines and other animals. The following discusses the apparatus applied to an equine, although it will be recognized that this discussion also applies to apparatuses used with other animals.

A first embodiment is associated with equine's limbs, either forequarter of hindquarter. This first embodiment includes an upper apparatus unit and a lower apparatus unit. Each unit includes a power source, a microprocessor, a TE device, and a power unit, as shown, for example, in FIG. 6. The upper unit is attachable to the upper limb of the equine and can be used to treat inflammation to the to the cannon bone, digital flexor, superficial flexor tendon, deep flexor tendon and/or extensor tendon. The lower unit is attachable to the lower limb of the equine and can be used to treat the proximal sesamoid bones, suspensory ligament, and/or distal sesamoidian ligaments. Other conditions, such as laminitis, can be aided by use of the lower unit.

A second embodiment is mounted to the equine's back to provide relief to strain or injury of the equine's back. In this second embodiment, a single or several, independently functioning sub-unit apparatuses can be embedded into a horse blanket, for example, opposite the equine's back/spine and flanks. Each sub-unit apparatus comprises a power unit, microprocessor, TE device, and a power switch, as shown, for example, in FIG. 6. In addition, various sensors can be located in the horse blanket to detect the horse's vital signs, such as blood pressure, heart rate, and breathing rate. Measuring the equine's vital signs during all types of equine activity assists in determining possible medical problems. Because the sub-unit apparatus(es) are mounted to the horse blanket, the equine may move freely without any restrictions, and the microprocessor can monitor the vital signs independent of the type of activity. This allows for a realistic evaluation of the equine and minimizes muscle atrophy of the equine, which is associated with confinement in a stall for long periods of time.

In another aspect of the invention, remote, automated application(s) of drug(s)/agent(s) to the equine is possible. Providing an accurate dosage at the correct time and in the proper configuration maximizes effectiveness of the drug/agent with the least adverse effects. Adverse movements of the equine are factored into the administration of the drug (s)/agent(s). Further, multiple drugs/agents can be given to the equine at prescribed times and in the prescribed amounts.

In a further aspect of the invention, electrodes may be mounted to the horse blanket or limb and connected to the microprocessor to provide electrical stimulation to the equine. The electrical stimulation can provide pain relief and/or healing of soft tissue or wounds and can be applied to specific locations, dependent upon the location of the electrodes.

The apparatus can also be designed to monitor the movement of the equine's limbs during exercise or pasture roaming. The apparatus allows for the determination of movement of individual, some, or all of the equine's limbs simultaneously in order to ascertain if there are any problems in the equine's movements in a natural environment, allowing for an improved evaluation of the equine.

The apparatus can include a central microprocessor that communicates with microprocessors of the various apparatus sub-units mounted limbs and/or horse blanket. The central microprocessor can collect the data acquired by the microprocessor(s) of the apparatus sub-units, in either real-time or as data pre-recorded by the microprocessors of the apparatus sub-units. The central microprocessor and the microprocessors of the apparatus sub-units can communicate via wireless communication data links or via a high-density digital recorder mounted to the horse blanket. The data gathered by the central microprocessor can then be sent to a remote computer to evaluate the equine to determine what medical conditions, if any, exist, to prescribe medical regimes, and to monitor the medical treatment. Thus, the apparatus has minimal negative impact on the equine and maximum therapeutic value.

In describing the invention, reference has been made to a preferred embodiment and illustrative advantages of the invention. Those skilled in the art, however, and familiar with the instant disclosure of the subject invention, may recognize the numerous other modifications, variations, and adaptations may be made without departing from the scope of the invention.

What is claimed is:

1. An apparatus for providing at least one of therapeutic heating and cooling to a body surface comprising:
    a wrap adapted to be secured to said body surface, said wrap including an outer layer facing away from said body surface and an inner layer facing toward said body surface when said wrap is so secured, first and second elastic layers positioned between said inner and outer layers, and first and second conductive layers positioned between said first and second elastic layers;
    at least one temperature sensor mounted to said inner layer for measuring an actual temperature of said body surface;
    at least one TE device mounted between said first and second conductive layers to selectively deliver heat to and remove heat from said body surface; and
    a control unit mounted to said outer layer for receiving the actual temperature of said body surface from each said temperature sensor and for communication with each said TE device to operate the same as one of a heater and a cooler thereby achieving a desired temperature of said body surface.

2. The apparatus of claim 1 further comprising a pressure sensor mounted to said wrap, said pressure sensor adapted to turn ON said control unit when said pressure sensor is activated.

3. The apparatus of claim 1, further including a strap, said strap mounted on the outer surface of said outer layer and adapted to attach said wrap to said body surface.

4. The apparatus of claim 1, wherein said wrap further includes first and second insulate layers, said insulate layers positioned between said first and second conductive layers, on opposite sides of and contacting each said TE device.

5. The apparatus of claim 4, wherein said first and second elastic layers are formed of a ventilatory material.

6. The apparatus of claim 4, further comprising first cavity means for receipt of fluid located between and formed by said second insulate layer.

7. The apparatus of claim 6, wherein said first cavity means comprises two smaller cavities, and a fluid passage connecting said smaller cavities.

8. The apparatus of claim 4, further comprising second cavity means for receipt of fluid located between and formed by said first insulate layer.

9. The apparatus of claim 8, wherein said second cavity means comprises two smaller cavities, and a fluid passage connecting said smaller cavities.

10. The apparatus of claim 4 further comprising a wiring/tubing layer disposed between said first and second insulate layers, each said TE device connected to said wiring/tubing layer, and each said temperature sensor being positioned on the outer surface of said inner layer.

11. The apparatus of claim 10, further comprising at least one pressure sensor disposed on said outer surface of said inner layer.

12. The device of claim 10, further comprising an electrical stimulation unit, said electrical stimulation unit connected to said microprocessor for delivery of an electrical pulse to said body surface.

13. The device of claim 12, wherein said electrical stimulation unit comprises a waveform generator connected to said microprocessor, a modulator unit connected to said waveform generator, a driver connected to the modulator, and at least one electrode connected to said driver to deliver the electrical pulse to the body surface.

14. The apparatus of claim 4 further comprising a wiring/tubing layer disposed between said first and second insulate layers, each said TE device connected to said wiring/tubing layer, and wherein said inner layer comprises a fluid transfer medium with each said temperature sensor being mounted to said fluid transfer medium.

15. The apparatus of claim 14 further comprising a cavity layer providing at least one expandable cavity for filling with fluid, said cavity layer disposed between said wiring/tubing layer and one of said first and second insulate layers.

16. The apparatus of claim 4, wherein said wrap further includes a wiring/tubing layer positioned between said first and second insulate layers.

17. The apparatus of claim 15, wherein each said TE device is embedded in said wiring/tubing layer.

18. The apparatus of claim 1, further comprising at least one electrode mounted to said lower layer for receipt of information from said control unit and for transmission of an electric pulse to the body surface.

19. The apparatus of claim 1, further comprising at least one pressure sensor mounted to said wrap for receipt of information from said control unit.

20. The apparatus of claim 1, further comprising at least one electrode mounted to said wrap for receipt of information from said control unit and for transmission of an electric pulse to said body surface.

21. The apparatus of claim 1, wherein each said TE device comprises a Peltier device.

22. The apparatus of claim 1, further comprising at least one pressure sensor disposed on the inner surface of said inner layer.

23. The apparatus of claim 1, further comprising at least one electrode disposed on the inner surface of said inner layer.

24. The apparatus of claim 23, further comprising at least one pouch disposed on the inner surface of said inner layer for placement of at least one electrode.

25. The apparatus of claim 24, further comprising a template for the location of each said electrode on said body surface, and the appropriate pouch disposed on the inner surface of said inner layer.

26. A device for achieving a desired temperature of a body surface comprising:
- a power source;
- at least one temperature sensor that detects an actual temperature on said body surface;
- a controller, said controller comprising a microprocessor having memory that stores at least one program for adjusting said desired temperature over time;
- a first switch responsive to said actual temperature detected by any of said temperature sensors that turns OFF said power source when said actual temperature is either above a maximum or below a minimum temperature;
- at least one TE device connected to receive a signal from said controller corresponding to said desired temperature and to deliver at least one of heating and cooling to said body surface in response to said desired temperature;
- a second switch electrically communicating with each said TE device and adapted to operate each said TE device to which it is connected to deliver heating or cooling;
- an electrical stimulation unit connected to said microprocessor for delivery of an electrical pulse to said body surface; and
- an ionthophoresis unit connected to said microprocessor for delivery of medication to said body surface.

27. The device of claim 26, wherein said iontophoresis unit comprises a medication interface connected to said microprocessor, a medication controller unit connected to said medication interface, a medication dispenser connected to said medication controller, and at least one special electrode connected to said medication dispenser to deliver said medication to said body surface.

28. A device for achieving a desired temperature of a body surface comprising:
- a power source;
- at least one temperature sensor that detects an actual temperature on said body surface;
- a controller, said controller comprising a microprocessor having memory that stores at least one program for adjusting said desired temperature over time;
- a first switch responsive to said actual temperature detected by any of said temperature sensors that turns OFF said power source when said actual temperature is either above a maximum or below a minimum temperature;
- at least one TE device connected to receive a signal from said controller corresponding to said desired temperature and to deliver at least one of heating and cooling to said body surface in response to said desired temperature;
- a second switch electrically communicating with each said TE device and adapted to operate each said TE device to which it is connected to deliver one of heating or cooling; and
- a heart rate sensor unit comprising an ultra miniature microphone connected to a preamp, an active switched capacitor filter connected to said preamp, at least one amplifier connected to said active switched capacitor filter, at least one digitizer connected to said amplifier, and a microprocessor connected to each said digitizer.

29. The device of claim 28, further comprising a data link claim unit connected to said microprocessor for transfer of information to and from said microprocessor.

30. The device of claim 29, wherein said data link unit comprises an input/output interface connected to said microprocessor, a data input/output processor and an input/output connector connected to said input/output interface, and a transceiver connected to said input/output processor to transfer data to a remote computer.

31. The device of claim 29, further comprising a remote computer unit, connected to said device, for processing of information to and from the apparatus microprocessor.

32. The device of claim 31, wherein said remote computer unit comprises a transceiver connected to said signal processor, an input/output unit connected to said signal processor, and a computer connected to said input/output unit to process and transfer data to the apparatus.

33. An apparatus for providing a therapeutic treatment to the body surface, comprising:
- a wrap adapted to be secured to the body surface;
- at least one temperature sensor mounted to said wrap to measure an actual temperature of the body surface;
- at least one TE device mounted to said wrap to selectively deliver heat to and remove heat from the body surface;
- at least one electrode mounted to said wrap to deliver an electrical pulse to the body surface;
- at least one special electrode mounted to said wrap to deliver medication to the body surface;

a controller mountable to said wrap for receiving the actual temperature of the body surface from said at least one temperature sensor and for communication with said at least one TE device and said at least one electrode and said at least one special electrode simultaneously, thereby simultaneously medicating, electrically stimulating, and selectively delivering heat to and removing heat from the body surface.

34. A device for achieving a desired temperature of a body surface comprising:

a power source;

at least one temperature sensor that detects an actual temperature on said body surface;

a controller, said controller comprising a microprocessor having a memory that stores at least one program for adjusting said desired temperature, said microprocessor connected to at least one breathing rate sensor for receipt of a signal indicative of an actual breathing rate of the user;

a first switch responsive to said actual temperature detected by any of said temperature sensors that turns OFF said power source when said actual temperature is either above a maximum or below a minimum temperature;

at least one TE device connected to receive a signal from said controller corresponding to said desired temperature and to deliver at least one of heating and cooling to said body surface in response to said desired temperature; and a second switch electrically communicating with each said TE device and adapted to operate each said TE device to which it is connected to deliver one of heating or cooling.

35. A device for achieving a desired temperature of a body surface comprising:

a power source;

at least one temperature sensor that detects an actual temperature on said body surface;

a controller, said controller comprising a microprocessor having memory that stores at least one program for adjusting said desired temperature over time;

a first switch responsive to said actual temperature detected by any of said temperature sensors that turns OFF said power source when said actual temperature is either above a maximum or below a minimum temperature;

at least one TE device connected to receive a signal from said controller corresponding to said desired temperature and to deliver at least one of heating and cooling to said body surface to return said body surface to said desired temperature;

a second switch electrically communicating with each said TE device and adapted to operate each said TE device to which it is connected to deliver one of heating and cooling;

an electrical stimulation unit connected to said microprocessor for delivery of an electrical pulse to said body surface, said electrical stimulation unit comprising a waveform generator connected to said microprocessor, a modulator unit connected to said waveform generator, a driver connected to said modulator, and at least one electrode connected to said driver to deliver said electrical pulse to said body surface; and an evoked response detection unit comprising an ultra miniature microphone connected to a preamp, an active switched capacitor filter connected to said preamp, at least one amplifier connected to said active switched capacitor filter, at least one digitizer connected to said amplifier, and a microprocessor connected to said digitizer.

* * * * *